(12) United States Patent
Berggren et al.

(10) Patent No.: US 9,068,971 B2
(45) Date of Patent: Jun. 30, 2015

(54) METHODS FOR TREATING AND/OR LIMITING DEVELOPMENT OF DIABETES

(71) Applicant: BioCrine AB, Stockholm (SE)

(72) Inventors: Per Olof Berggren, Solna (SE); Shao-Nian Yang, Stockholm (SE)

(73) Assignee: BioCrine AB, Stockholm (SE)

( * ) Notice: Subject to any disclaimer, the term of this patent is extended or adjusted under 35 U.S.C. 154(b) by 0 days.

(21) Appl. No.: 14/108,597

(22) Filed: Dec. 17, 2013

(65) Prior Publication Data

US 2014/0170113 A1 Jun. 19, 2014

Related U.S. Application Data

(60) Provisional application No. 61/738,835, filed on Dec. 18, 2012.

(51) Int. Cl.
*A01N 1/02* (2006.01)
*C12N 5/00* (2006.01)
*G01N 33/50* (2006.01)

(52) U.S. Cl.
CPC ............ *G01N 33/502* (2013.01); *G01N 33/507* (2013.01); *G01N 2333/705* (2013.01); *G01N 2333/775* (2013.01)

(58) Field of Classification Search
CPC .......................... G01N 33/5041; G01N 33/507
See application file for complete search history.

(56) References Cited

U.S. PATENT DOCUMENTS

| | | |
|---|---|---|
| 2004/0171073 A1 | 9/2004 | Neiland et al. |
| 2004/0224304 A1 | 11/2004 | Berggren et al. |

FOREIGN PATENT DOCUMENTS

| | | |
|---|---|---|
| WO | 2009/128734 | 10/2009 |
| WO | 2013/000920 | 1/2013 |

OTHER PUBLICATIONS

International Search Report PCT/EP2013/076917, mailed Feb. 27, 2014.
Juntti-Berggren, et al. (2004) "Apolioprotein CIII promotes Ca2+-dependent beta cell death in type 1 diabetes," Proc Natl Acad Sci USA, 101(27):10090-10094.
Holmberg, et al. (2011) "Lowering apolipoprotein CIII delays onset of type 1 diabetes," Proc Natl Acad Sci USA, 108(26): 10685-10689.
Yang, et al. (2006) "The role of voltage-gated calcium channels in pancreatic beta-cell physiology and pathophysiology," Endocr Rev, 27(6):621-676.
Shi, et al. (2013) "Apolipoprotein CIII hyperactivates [beta] cell CaV1 channels through SR-B1/[beta]1 integrin-dependent coactivation of PKA and Src," Cell Mol Life Sci, pp. 1-15.
Murao, et al. "Interferon alpha decreases expression of human scavenger receptor class BI, a possible HCV receptor in hepatocytes," Gut. May 2008;57(5):664-71. Epub Nov. 12, 2007.
Kitayama, et al., "Blockade of scavenger receptor class B type I raises high density lipoprotein cholesterol levels but exacerbates atherosclerotic lesion formation in apolipoprotein E deficient mice.," J Pharm Pharmacol. Dec. 2006;58(12):1629-38.
Cejvan et al.,(2003) "Intra-islet somatostatin regulates glucagon release via type 2 somatostatin receptors in rats," Diabetes 52:1176-1181.
Fagan et al., (1998) "Insulin Secretion is inhibited by subtype five somatostatin receptor in the mouse," Surgery 124:254-259.
Zambre et al., (1999) "Inhibition of human pancreatic islet insulin release by receptor-selective somatostatin analogs directed to somatostatin receptor subtype-5," Biochem. Pharmacol. 57:1159-1164.
Yang, S. N. & Berggren, P. O. b-Cell CaV channel regulation in physiology and pathophysiology. Am. J. Physiol. 288, E16-E28 (2005).
Catterall, W. A. Structure and regulation of voltage-gated Ca2+ channels. Annu. Rev. Cell Dev. Biol. 16, 521-555 (2000).
Juntti-Berggren, L. et al. Increased activity of L-type Ca2+ channels exposed to serum from patients with type I diabetes. Science 261, 86-90 (1993).
Sol, E. M., Sundsten, T. & Bergsten, P. Role of MAPK in apolipoprotein CIII-induced apoptosis in INS-1E cells. Lipids Health Dis. 8, 3 (2009).
Gangabadage, C. S. et al. Structure and dynamics of human apolipoprotein CIII. J. Biol. Chem. 283, 17416-17427 (2008).
Jong, M. C., Hofker, M. H. & Havekes, L. M. Role of ApoCs in lipoprotein metabolism: functional differences between ApoC1, ApoC2, and ApoC3. Arterioscler. Thromb. Vasc. Biol. 19, 472-484 (1999).
Xu, S. et al. Apolipoproteins of HDL can directly mediate binding to the scavenger receptor SR-BI, an HDL receptor that mediates selective lipid uptake. J. Lipid Res. 38, 1289-1298 (1997).
Clavey, V., Lestavel-Delattre, S., Copin, C., Bard, J. M. & Fruchart, J. C. Modulation of lipoprotein B binding to the LDL receptor by exogenous lipids and apolipoproteins CI, CII, CIII, and E. Arterioscler. Thromb. Vasc. Biol. 15, 963-971 (1995).
Huard, K. et al. Apolipoproteins C-II and C-III inhibit selective uptake of low- and high-density lipoprotein cholesteryl esters in HepG2 cells. Int. J. Biochem. Cell Biol. 37, 1308-1318 (2005).
Chan, D. C., Watts, G. F., Redgrave, T. G., Mori, T. A. & Barrett, P. H. Apolipoprotein B-100 kinetics in visceral obesity: associations with plasma apolipoprotein C-III concentration. Metabolism 51, 1041-1046 (2002).
Sundsten, T., Ostenson, C. G. & Bergsten, P. Serum protein patterns in newly diagnosed type 2 diabetes mellitus—influence of diabetic environment and family history of diabetes. Diabetes Metab. Res. Rev. 24, 148-154 (2008).
Atzmon, G. et al. Lipoprotein genotype and conserved pathway for exceptional longevity in humans. PLoS Biol. 4, e113 (2006).
Kawakami, A. et al. Apolipoprotein CIII in apolipoprotein B lipoproteins enhances the adhesion of human monocytic cells to endothelial cells. Circulation 113, 691-700 (2006).

(Continued)

*Primary Examiner* — Daniel C Gamett
(74) *Attorney, Agent, or Firm* — McDonnell Boehnen Hulbert & Berghoff LLP

(57) ABSTRACT

The present invention provides methods for identifying candidate compounds for limiting development of and/or treating diabetes, and methods for limiting development of and/or treating diabetes.

10 Claims, 9 Drawing Sheets

(56) References Cited

OTHER PUBLICATIONS

Fang, D. Z. & Liu, B. W. Apolipoprotein C-III can specifically bind to hepatic plasma membranes. Mol. Cell. Biochem. 207, 57-64 (2000).

Kawakami, A. et al. Apolipoprotein CIII-induced THP-1 cell adhesion to endothelial cells involves pertussis toxin-sensitive G protein- and protein kinase Ca-mediated nuclear factor-kB activation. Arterioscler. Thromb. Vasc. Biol. 27, 219-225 (2007).

Rueckschloss, U. & Isenberg, G. Contraction augments L-type Ca2+ currents in adherent guinea-pig cardiomyocytes. J. Physiol. 560, 403-411 (2004).

Waitkus-Edwards, K. R. et al. a4b1 Integrin activation of L-type calcium channels in vascular smooth muscle causes arteriole vasoconstriction. Circ. Res. 90, 473-480 (2002).

Wu, X., Davis, G. E., Meininger, G. A., Wilson, E. & Davis, M. J. Regulation of the L-type calcium channel by a5b1 integrin requires signaling between focal adhesion proteins. J. Biol. Chem. 276, 30285-30292 (2001).

Gui, P. et al. Integrin receptor activation triggers converging regulation of Cav1.2 calcium channels by c-Src and protein kinase A pathways. J. Biol. Chem. 281, 14015-14025 (2006).

Bamberger, M. E., Harris, M. E., McDonald, D. R., Husemann, J. & Landreth, G. E. A cell surface receptor complex for fibrillar beta-amyloid mediates microglial activation. J. Neurosci. 23, 2665-2674 (2003).

Ristic, H., Srinivasan, S., Hall, K. E., Sima, A. A. & Wiley, J. W. Serum from diabetic BB/W rats enhances calcium currents in primary sensory neurons. J. Neurophysiol. 80, 1236-1244 (1998).

Kavalali, E. T., Hwang, K. S. & Plummer, M. R. cAMP-dependent enhancement of dihydropyridine-sensitive calcium channel availability in hippocampal neurons. J. Neurosci. 17, 5334-5348 (1997).

Yang, J. & Tsien, R. W. Enhancement of N- and L-type calcium channel currents by protein kinase C in frog sympathetic neurons. Neuron 10, 127-136 (1993).

Mukai, E. et al. Exendin-4 suppresses Src activation and reactive oxygen species production in diabetic Goto-Kakizaki rat islets in an Epac-dependent manner. Diabetes 60, 218-226 (2011).

Kantengwa, S. et al. Identification and characterization of a3b1 integrin on primary and transformed rat islet cells. Exp. Cell Res. 237, 394-402 (1997).

Bosco, D., Meda, P., Halban, P. A. & Rouiller, D. G. Importance of cell-matrix interactions in rat islet b-cell secretion in vitro: role of a6b1 integrin. Diabetes 49, 233-243 (2000).

Nikolova, G. et al. The vascular basement membrane: a niche for insulin gene expression and b cell proliferation. Dev. Cell 10, 397-405 (2006).

Luo, B. H., Carman, C. V. & Springer, T. A. Structural basis of integrin regulation and signaling. Annu. Rev. Immunol. 25, 619-647 (2007).

Figure 5
a
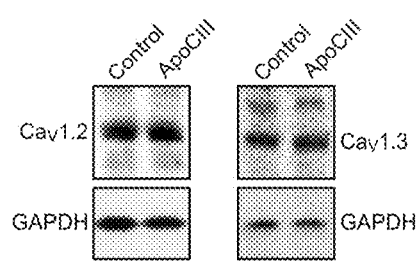
b
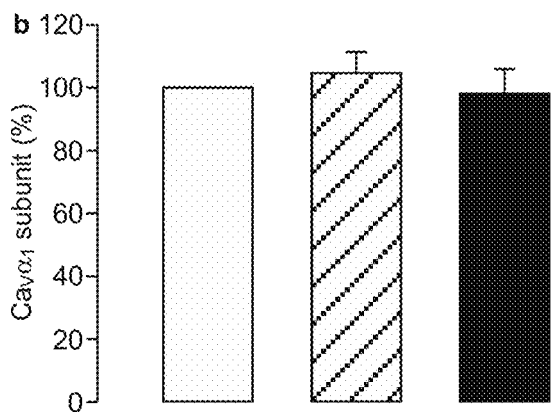

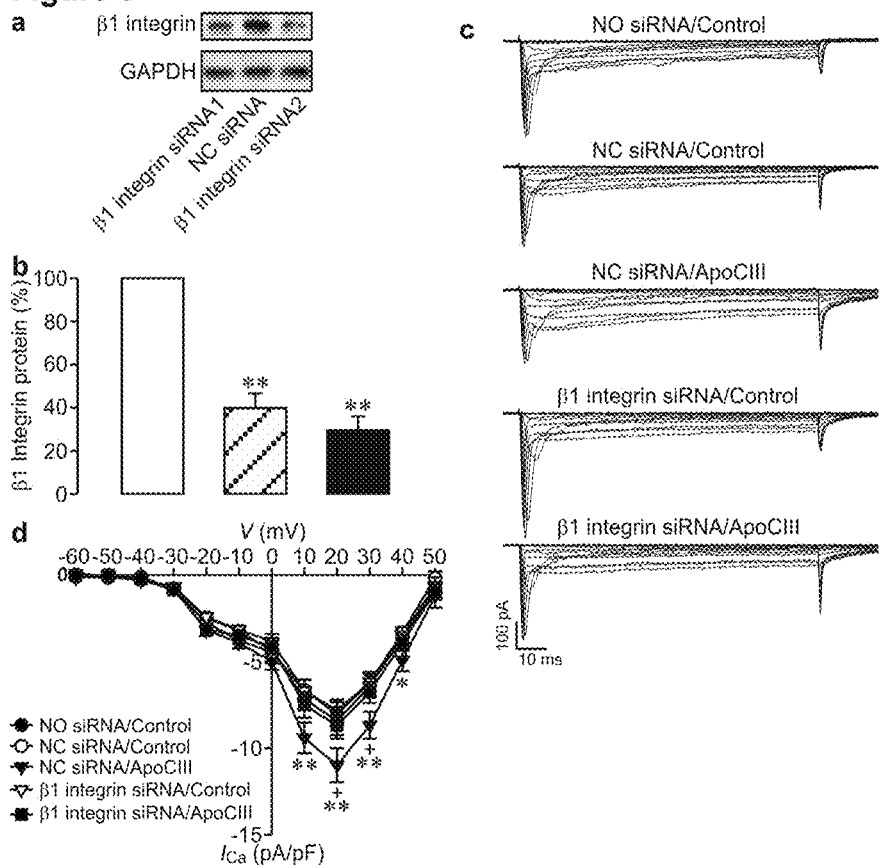

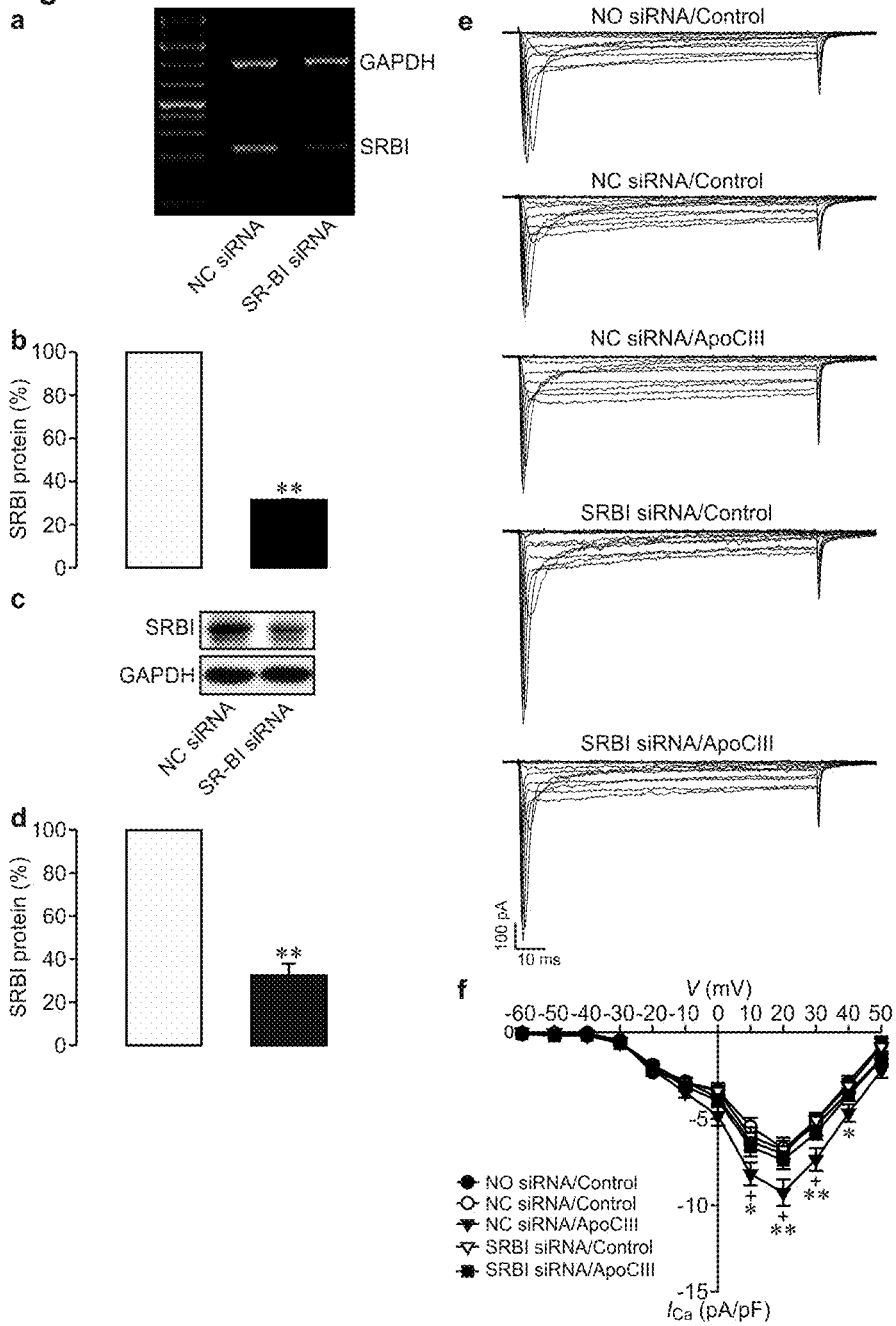

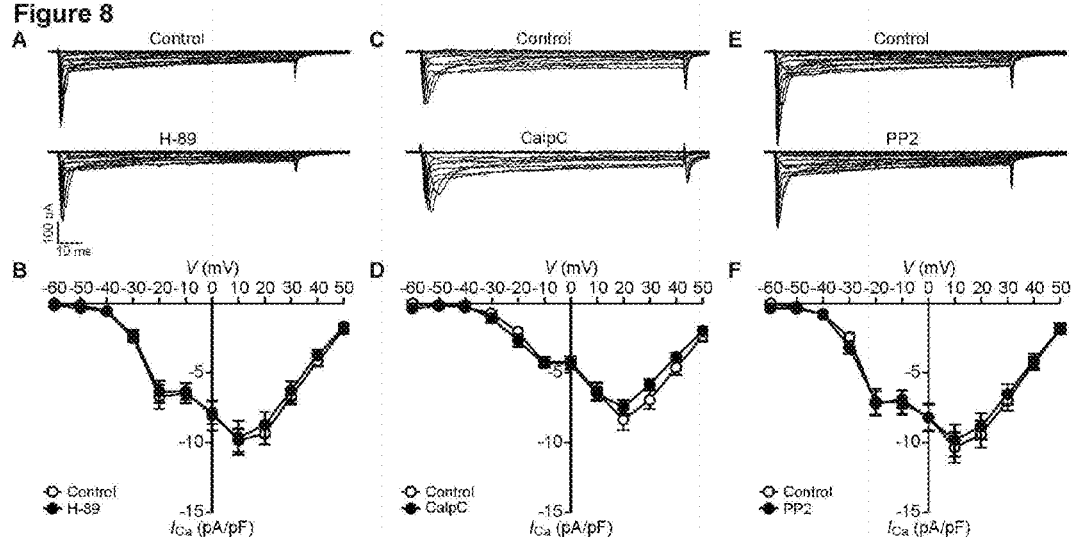

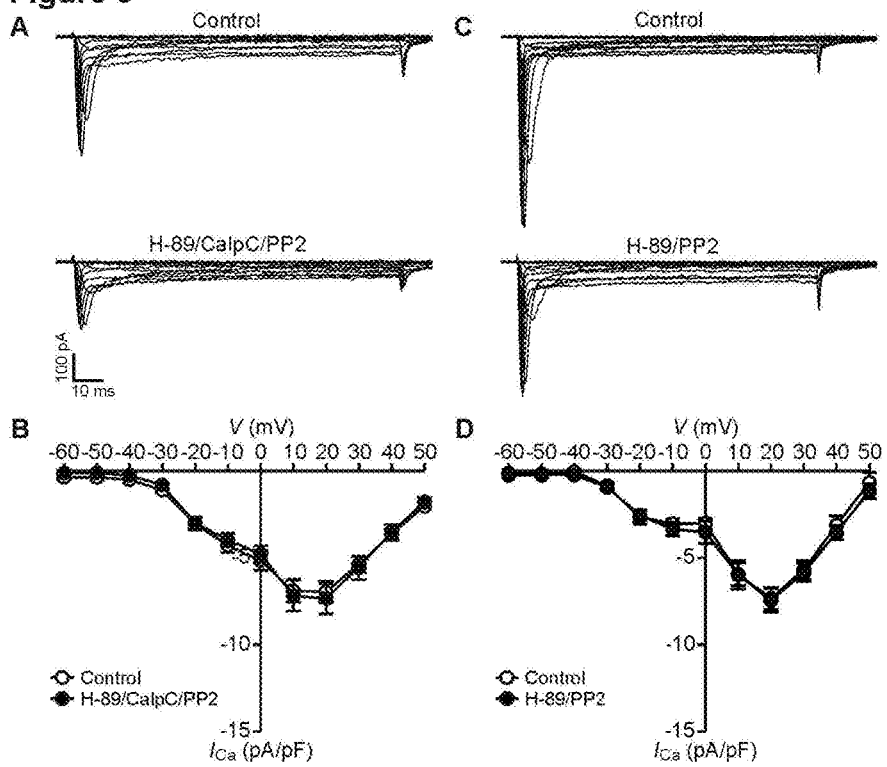

METHODS FOR TREATING AND/OR LIMITING DEVELOPMENT OF DIABETES

CROSS-REFERENCE

This application claims priority to U.S. Provisional Patent Application Ser. No. 61/738,835, filed Dec. 18, 2012, incorporated by reference herein in its entirety.

INTRODUCTION

Voltage-gated calcium ($Ca_V$) channels are critical in β cell physiology and pathophysiology. They not only take center stage in the regulation of insulin secretion, but are also involved in β cell development, survival and growth through the regulation of protein phosphorylation, gene expression and the cell cycle. The function and density of β cell $Ca_V$ channels are regulated by a wide range of mechanisms either shared by other cell types or specific to β cells, e.g., channel phosphorylation, interaction with other molecules and glucose metabolism-derived signaling. Dysfunctional $Ca_V$ channels causes β cell malfunction and even death as manifested in the most common metabolic disorder diabetes mellitus. Indeed, a T-lymphocyte-mediated autoimmune attack plays a crucial role in β cell death in type 1 diabetes. In addition, factors in type 1 diabetic serum compel non-physiological amounts of $Ca^{2+}$ to enter pancreatic β cells through hyperactivation of β cell $Ca_V$ channels, resulting in β cell apoptosis. Undoubtedly, this process aggravates the disease development on top of the autoimmune attack. Such factors are also visualized in type 2 diabetic serum, where they behave in the same way as they do in type 1 diabetic serum. In fact, reduction in β cell mass and hyperactivation of β cell $Ca_V$ channels appear under type 2 diabetic conditions such as those in the Goto-Kakizaki rat.

SUMMARY OF THE INVENTION

In a first aspect, the present invention provides methods for identifying candidate compounds for limiting development of and/or treating diabetes, comprising
  (a) contacting a first population of insulin secreting cells with an amount of apolipoprotein CIII (ApoCIII) effective to increase density and/or conductivity of $Ca_v1$ channels, in the presence of one or more test compounds;
  (b) contacting a second population of insulin secreting cells with an amount of ApoCIII effective to increase density and/or conductivity of $Ca_v1$ channels, in the presence of the one or more test compounds, and further contacting the second population of insulin secreting cells with a molecule that inhibits scavenger receptor class B type I (SRBI) expression or activity; and
  (c) identifying positive test compounds that inhibit the ApoCIII-induced increase in density and/or conductivity of $Ca_v1$ channels in the first population of insulin secreting cells to a greater degree than in the second population of insulin secreting cells as candidate compounds for limiting development of and/or treating diabetes.

In one embodiment, the method further comprises contacting a third population of insulin secreting cells with an amount of ApoCIII effective to increase density and/or conductivity of $Ca_v1$ channels, in the presence of one or more of the candidate compounds, and further contacting the third population of insulin secreting cells with a $Ca_v2$ and/or $Ca_v3$ channel blocker, wherein the candidate that inhibit the ApoCIII-induced increase in density and/or conductivity in the third population of insulin secreting cells to a greater degree than in the first population of insulin secreting cells are preferred candidate compounds for limiting development of and/or treating diabetes.

In a further embodiment that can be combined with any of the embodiments herein, the method further comprises contacting a fourth population of insulin secreting cells with an amount of ApoCIII effective to increase density and/or conductivity of $Ca_v1$ channels, in the presence of one or more of the candidate compounds and further contacting the fourth population of insulin secreting cells with a Src kinase inhibitor and/or a protein kinase A (PKA) inhibitor, wherein those candidate compounds that inhibit the ApoCIII-induced increase in density and/or conductivity of $Ca_v1$ channels in the first population of insulin secreting cells to a greater degree than in fourth population of insulin secreting cells are preferred candidate compounds for limiting development of and/or treating diabetes.

In another embodiment that can be combined with any of the embodiments herein, the methods further comprises contacting a fifth population of insulin secreting cells with an amount of ApoCIII effective to density and/or conductivity of $Ca_v1$ channels, in the presence of one or more of the candidate compounds, and further contacting the fifth population of insulin secreting cells with a molecule that inhibits β1 integrin expression or activity, wherein those candidate compounds that inhibit the ApoCIII-induced increase in density and/or conductivity of $Ca_v1$ channels in the first population of insulin secreting cells to a greater degree than in the fifth population of insulin secreting cells are preferred candidate compounds for limiting development of and/or treating diabetes.

In a second aspect, the present invention provides methods for identifying candidate compounds for limiting development of and/or treating diabetes, comprising
  a) contacting a first population of insulin secreting cells with an amount of ApoCIII effective to increase density and/or conductivity of $Ca_v1$ channels, in the presence of one or more test compounds; and
  b) identifying those positive test compounds that inhibit SRBI expression or activity in the first population of insulin secreting cells compared to control, wherein the positive test compounds are candidate compounds for limiting development of and/or treating diabetes.

In one embodiment, the control comprises contacting a second population of insulin secreting cells contacted with an amount of ApoCIII effective to increase density and/or conductivity of $Ca_v1$ channels, in the absence of one or more test compounds. This embodiment may comprise, for example, contacting the second population of cells with a formulation, such as a buffer, that is similar to or identical to the formulation the test compounds are dissolved in.

In various embodiments of any of these aspects of the invention, each of which can be combined except as clearly dictated otherwise by the context, the method comprises contacting the cells with ApoCIII for at least 6 hours; the candidate compounds are candidate compounds for limiting development of and/or treating type 1 diabetes; and/or wherein the candidate compounds are candidate compounds for limiting development of and/or treating type 2 diabetes.

In a third aspect, the present invention provides methods for treating or limiting development of diabetes, comprising administering to a subject in need thereof with an amount effective of an inhibitor of SRBI expression and/or activity. In various embodiments, the inhibitor is selected from the group consisting of anti-SRBI antibodies, anti-SRBI aptamers, SRBI siRNAs, SRBI shRNAs, SRBI antisense oligonucleotides, and small molecules that inhibit SRBI expression and/or activity.

DESCRIPTION OF THE FIGURES

FIG. 5. Apolipoprotein CIII incubation does not alter β cell $Ca_V1$ channel expression. (a) Representative immunoblots of RINm5F cell homogenates, subjected to incubation with vehicle as control or apolipoprotein CIII (ApoCIII), probed with anti-$Ca_V1.2$, anti-$Ca_V1.3$ and anti-GAPDH antibodies, respectively. (b) Immunoblot quantification of the relative abundance of $Ca_V1.2$ (hatched column, n=6) and $Ca_V1.3$ subunits (filled column, n=6) in RINm5F cell homogenates subjected to ApoCIII incubation in comparison with control (open column, n=6). There was no significant difference in the relative abundance of total $Ca_V1.2$ and $Ca_V1.3$ subunits between control cells and cells incubated with ApoCIII ($P>0.05$).

FIG. 6. Knockdown of β1 integrin abrogates apolipoprotein CIII-induced exaggeration of whole-cell $Ca^{2+}$ currents in RINm5F cells. (a) Representative blots of β1 integrin- and GAPDH-immunoreactive bands in β1 integrin siRNA #1-, negative control siRNA (NC siRNA)- and β1 integrin siRNA #2-transfected cells. (b) Immunoblot quantifications of β1 integrin protein in NC siRNA- (open column, n=6), β1 integrin siRNA #1- (hatched column, n=6) and β1 integrin siRNA #2-transfected RINm5F cells (filled column, n=6). **$P<0.01$ versus NC siRNA. (c) Sample whole-cell $Ca^{2+}$ current traces registered in individual cells following mock transfection and incubation with control vehicle (NO siRNA/Control, cell capacitance: 12.1 pF), NC siRNA transfection and control vehicle treatment (NC siRNA/Control, cell capacitance: 11.4 pF), NC siRNA transfection and apolipoprotein CIII (ApoCIII) incubation (NC siRNA/ApoCIII, cell capacitance: 12.1 pF), β1 integrin siRNA transfection and exposure to vehicle solution (β1 integrin siRNA/Control, cell capacitance: 11.9 pF) and β1 integrin siRNA transfection and ApoCIII exposure (β1 integrin siRNA/ApoCIII, cell capacitance: 12.4 pF), respectively. (d) $Ca^{2+}$ current density-voltage relationships in cells subjected to NO siRNA/Control (filled circles, n=29), NC siRNA/Control (open circles, n=28), NC siRNA/apoCIII (filled triangles, n=28), β1 integrin siRNA/Control (open triangles, n=29) and β1 integrin siRNA/ApoCIII (filled squares, n=29). *$P<0.05$ and **$P<0.01$ versus NO siRNA/Control, NC siRNA/Control and β1 integrin siRNA/Control. +P<0.05 versus β1 integrin siRNA/ApoCIII.

FIG. 7. Knockdown of SRBI prevents apolipoprotein CIII-induced enhancement of whole-cell $Ca^{2+}$ currents in RINm5F cells. (a) Representative blots of GAPDH- and GAPDH-mRNA bands in SRBI siRNA- and negative control siRNA (NC siRNA)-transfected cells. (b) Quantitative immunoblot measurements of SRBI protein in NC siRNA- (open column, n=6) and SRBI siRNA-transfected RINm5F cells (filled column, n=6). P<0.01 versus NC siRNA. (c) Sample blots of SRBI- and GAPDH-immunoreactive bands in SRBI siRNA- and negative control siRNA (NC siRNA)-transfected cells. (d) Quantifications of SRBI mRNA in NC siRNA- (open column, n=7) and SRBI siRNA-transfected RINm5F cells (filled column, n=7). P<0.01 versus NC siRNA. (e) Representative whole-cell $Ca^{2+}$ current traces from individual cells subsequent to mock transfection and incubation with control vehicle (NO siRNA/Control, cell capacitance: 13.87 pF), NC siRNA transfection and control vehicle treatment (NC siRNA/Control, cell capacitance: 13.18 pF), NC siRNA transfection and apolipoprotein CIII (ApoCIII) incubation (NC siRNA/ApoCIII, cell capacitance: 13.53 pF), SRBI siRNA transfection and exposure to vehicle solution (SRBI siRNA/Control, cell capacitance: 12.90 pF) and SRBI siRNA transfection and ApoCIII exposure (SRBI siRNA/ApoCIII, cell capacitance: 13.01 pF), respectively. (f) $Ca^{2+}$ current density-voltage relationships in cells subjected to NO siRNA/Control (filled circles, n=30), NC siRNA/Control (open circles, n=29), NC siRNA/apoCIII (filled triangles, n=30), SRBI siRNA/Control (open triangles, n=29) and SRBI siRNA/ApoCIII (filled squares, n=30). *P<0.05 and **P<0.01 versus NO siRNA/Control, NC siRNA/Control and SRBI siRNA/Control. +P<0.05 versus SRBI siRNA/ApoCIII.

FIG. 8. PKA, PKC or Src kinase inhibition does not alter whole-cell $Ca^{2+}$ currents in RINm5F cells under basal conditions. (a) Sample whole-cell $Ca^{2+}$ current traces from a vehicle-treated cell as control (cell capacitance: 8.8 pF) and a cell exposed to H-89 (cell capacitance: 8.5 pF). (b) Average $Ca^{2+}$ current density-voltage relationships in control cells (open circles; n=20) and cells incubated with H-89 (filled circles, n=20). (c) Sample whole-cell $Ca^{2+}$ current traces recorded in a control cell (cell capacitance: 10.4 pF) and a cell subjected to calphostin C incubation (CalpC, cell capacitance: 11.0 pF). (d) Average $Ca^{2+}$ current density-voltage relationships in control cells (open circles; n=29) and cells exposed to CalpC (filled circles, n=29). (e) Sample whole-cell $Ca^{2+}$ current traces obtained in a control cell (cell capacitance: 9.0 pF) and a PP2-treated cell (cell capacitance: 9.1 pF). (I) Average $Ca^{2+}$ current density-voltage relationships in control cells (open circles, n=20) and cells incubated with PP2 (filled circles, n=19).

FIG. 9. Combined inhibition of PKA, PKC and Src kinase or coinhibition of PKA and Src kinase does not influence whole-cell $Ca^{2+}$ currents in RINm5F cells under basal conditions. (a) Sample whole-cell $Ca^{2+}$ current traces obtained in a cell incubated with vehicle solution as control (cell capacitance: 10.8 pF) and a cell treated with the protein kinase inhibitor cocktail composed of H-89, calphostin C and PP2 (H-89/CalpC/PP2, cell capacitance: 9.7 pF). (b) Average $Ca^{2+}$ current density-voltage relationships in control cells (open circles, n=30) and cells treated with H-89/CalpC/PP2 (filled circles, n=30). (c) Sample whole-cell $Ca^{2+}$ current traces obtained in a vehicle-treated cell as control (cell capacitance: 9.4 pF) and a cell treated with the protein kinase inhibitors H-89 and PP2 (H-89/PP2, cell capacitance: 9.1 pF). (d) Average $Ca^{2+}$ current density-voltage relationships in control cells (open circles, n=24) and cells treated with H-89/PP2 (filled circles, n=24).

DETAILED DESCRIPTION OF THE INVENTION

Figure 1:
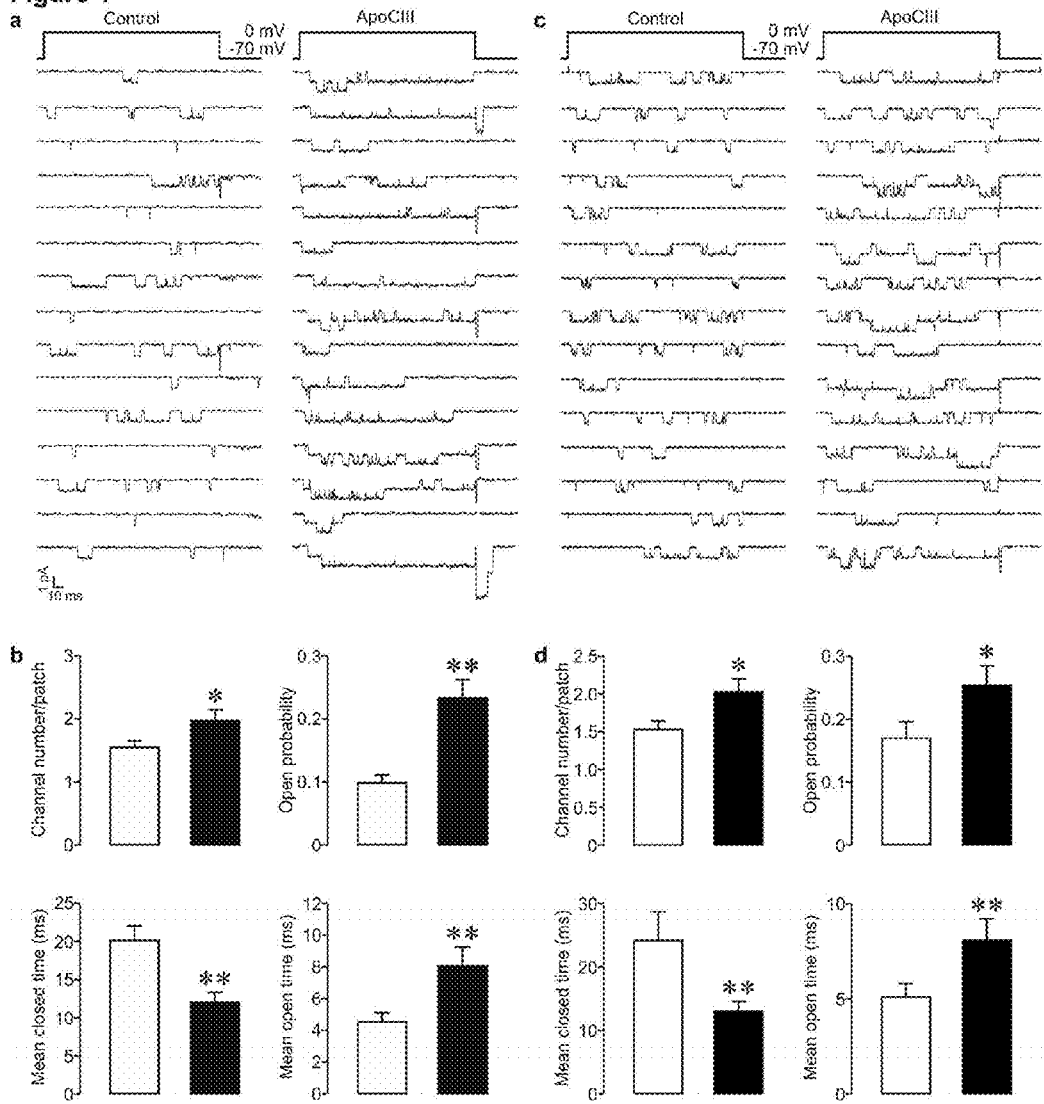
FIG. 1. Apolipoprotein CIII incubation increases both the density and conductivity of $Ca_V1$ channels in β cells. (a) Examples of unitary $Ca_V1$ channel currents detected in plasma membrane patches of mouse islet β cells incubated with either vehicle solution as control or apolipoprotein CIII (ApoCIII). (b) Average number, open probability, mean closed time and mean open time of unitary $Ca_V1$ channels measured in plasma membrane patches attached to mouse islet β cells exposed to either control vehicle (n=33) or ApoCIII (n=32). (c) Examples of unitary $Ca_V1$ channel currents recorded in plasma membrane patches attached to either a control RINm5F cell or a cell treated with ApoCIII. (d) Average number, open probability, mean closed time and mean open time of unitary $Ca_V1$ channels detected in plasma membrane patches of control RINm5F cells (n=34) or cells incubated with ApoCIII (n=35). *$P<0.05$ and **$P<0.01$ versus control.

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, 2nd Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number, respectively. Additionally, the words "herein," "above," and "below" and words of similar import, when used in this application, shall refer to this application as a whole and not to any particular portions of this application.

As used herein, the singular forms "a", "an" and "the" include plural referents unless the context clearly dictates otherwise. "And" as used herein is interchangeably used with "or" unless expressly stated otherwise.

All embodiments of any aspect of the invention can be used in combination, unless the context clearly dictates otherwise.

In a first aspect, the present invention provides methods for identifying candidate compounds for limiting development of and/or treating diabetes, comprising (a) contacting a first population of insulin secreting cells with an amount of apolipoprotein CIII (ApoCIII) effective to increase density and/or conductivity of $Ca_V 1$ channels, in the presence of one or more test compounds;

(b) contacting a second population of insulin secreting cells with an amount of ApoCIII effective to increase density and/or conductivity of $Ca_V 1$ channels, in the presence of the one or more test compounds, and further contacting the second population of insulin secreting cells with a molecule that inhibits scavenger receptor class B type I (SRBI) expression or activity, and (c) identifying positive test compounds that inhibit the ApoCIII-induced increase in density and/or conductivity of $Ca_V 1$ channels in the first population of insulin secreting cells to a greater degree than in the second population of insulin secreting cells as candidate compounds for limiting development of and/or treating diabetes.

The inventors have discovered that ApoCIII incubation caused significant increases in $Ca_V 1$ channel open probability and density at single channel levels. The treatment significantly enhanced whole-cell $Ca^{2+}$ currents and the $Ca_V 1$ channel blocker nimodipine completely abrogated the enhancement. The inventors have further discovered that knockdown of scavenger receptor class B type I (SRBI) prevented ApoCIII from hyperactivating β cell $Ca_V$ channels. Thus, inhibitors of SRBI should down-regulate positive candidate compounds of the present invention. Therefore, those positive test compounds that inhibit the ApoCIII-induced increase in density and/or conductivity of $Ca_v1$ channels in the first population of insulin secreting cells to a greater degree than in the second population of insulin secreting cells are candidate compounds for limiting development of and/or treating diabetes. Thus, the methods of this aspect of the invention can be used to identify compounds for limiting $Ca^{2+}$-dependent pancreatic β cell death in a specific manner, and thus for limiting development of and/or treating diabetes.

As used herein, "apoCIII" refers to a protein comprising the amino acid sequence shown in SEQ ID NO:2 (Human) (NCBI accession number CAA25233), SEQ ID NO:4 (Rat) (NCBI accession number, or SEQ ID NO:6 (Macaque) (NCBI accession number CAA48419), or functional equivalents thereof.

The apoCIII may be substantially purified apoCIII, available, for example, from Sigma Chemical Company (St. Louis, Mo.), wherein "substantially purified" means that it is removed from its normal in vivo cellular environment. Alternatively, the apoCIII may be present in a mixture, such as blood serum from type 1 diabetic or partially or fully purified therefrom using standard techniques, such as those described below. In a preferred embodiment, substantially purified apoCIII is used.

As discussed below, there are three known isoforms of human apoCIII that have the same amino acid sequence, but which differ in their glycosylation pattern. Thus, in a preferred embodiment, glycosylated apoCIII is used, wherein the glycosylation is preferably sialylation. In another preferred embodiment, mono-sialylated or di-sialylated apoCIII is used. Such glycosylated forms may be purchased, for example, from Sigma Chemical Company, or may be partially or fully purified using standard techniques, such as those described below.

Scavenger receptor class B member 1 (SRB1) also known as SR-BI, is encoded by the SCARB1 gene. SRBI is best known for its role in facilitating the uptake of cholesteryl esters from high-density lipoproteins in the liver.

The amino acid sequence of human SRBI is provided in SEQ ID NO:9. An exemplary cDNA nucleotide sequence is provided in SEQ ID NO: 10.

Any suitable molecule that inhibits SRBI expression (RNA or protein) or activity (including but not limited to SRBI blockade) can be used in the methods of the invention, including but not limited to anti-SRBI antibodies, anti-SRBI aptamers, SRBI siRNAs, SRBI shRNAs, SRBI antisense oligonucleotides, and small molecule SRBI inhibitors. Anti-SRBI antibodies are available from a variety of commercial suppliers, including ThermoFisher, Epitomics, and OriGene. In one embodiment, the inhibitor comprise interferon alpha, which has been shown to inhibit SRBI expression (Gut. 2008 May; 57(5):664-71. Epub 2007 Nov. 12). In another embodiment, the SRBI inhibitor comprises N-[4-(4-tert-Butoxycarbonylpiperazin-1-yl)phenyl]-(2-chloro-5-nitrophenyl)carboxamide (R-138329), which has been shown to block SRBI receptor activity (J Pharm Pharmacol. 2006 December; 58(12):1629-38). In another embodiment, the SRBI inhibitor comprises 2-Hexyl-1-cyclopentanone thiosemicarbazone, 33M20, BLT1, Block lipid transport-1, CAS Number 321673-30-7 (Available from Sigma Aldrich). In another embodiment, the SRBI inhibitor is any one or more of the SRBI inhibitors disclosed in US 20040171073 (incorporated by reference herein in its entirety); these compounds are noted in the US 20040171073 application (Tables 1-2) as compound numbers MIT 9952-1, 9952-2, 9952-3, 9952-4, 9952-5, 9952-6, 9952-7, 9952-8, 9952-9, 9952-10, 9952-11, 9952-12, 9952-13, 9952-14, 9952-15, 9952-16, 9952-17, 9952-18, 9952-19, 9952-20, 9952-21, 9952-22, 9952-23, 9952-24, 9952-25, 9952-26, 9952-27, 9952-28, 9952-29, 9952-30, 9952-31, 9952-32, 9952-33, 9952-34, 9952-35, 9952-36, 9952-37, 9952-38, 9952-39, 9952-40, 9952-41, 9952-42, 9952-43, 9952-44, 9952-45, 9952-46, 9952-47, 9952-48, 9952-49, 9952-50, 9952-51, 9952-52, 9952-53, 9952-54, 9952-55, 9952-56, 9952-57, 9952-58, 9952-59, 9952-60, 9952-61, 9952-62, 9952-63, 9952-64, 9952-65, 9952-66, 9952-67, 9952-68, 9952-69, 9952-70, 9952-71, 9952-72, 9952-73, 9952-74, 9952-75, 9952-76, 9952-77, 9952-78, 9952-79, 9952-80, 9952-81, 9952-82, 9952-83, 9952-84, 9952-85, 9952-86, 9952-87, 9952-88, 9952-89, 9952-90, 9952-91, 9952-92, 9952-93, 9952-94, 9952-95, 9952-96, 9952-97, 9952-98, 9952-99, 9952-100, 9952-101, 9952-102, 9952-103, 9952-104, 9952-105, 9952-106, 9952-107, 9952-108, 9952-109, 9952-110, 9952-111, 9952-112, 9952-113, 9952-114, 9952-115, 9952-116, 9952-117, 9952-118, 9952-119, 9952-120, 9952-121, 9952-122, 9952-123, 9952-124, 9952-125, 9952-126, 9952-127, 9952-128, 9952-129, 9952-130, 9952-131, 9952-132, 9952-133, 9952-134, 9952-135, 9952-136, 9952-137, 9952-138, 9952-139, 9952-140, 9952-141, 9952-142, 9952-143, 9952-144, 9952-145, 9952-146, 9952-147, 9952-148, 9952-149, 9952-150, 9952-151, 9952-152, 9952-153, 9952-154, 9952-155, 9952-156, 9952-157, 9952-158, 9952-159, 9952-160, 9952-161, 9952-162, 9952-163, 9952-164, 9952-165, 9952-166, 9952-167, 9952-168, 9952-169, 9952-170, 9952-171, 9952-172, 9952-173, 9952-174, 9952-175, 9952-176, 9952-177, 9952-178, 9952-179, 9952-180, 9952-181, 9952-182, 9952-183, 9952-184, 9952-185, 9952-186, 9952-187, 9952-188, 9952-189, 9952-190, 9952-191, 9952-192, 9952-193, 9952-194, 9952-195, 9952-196, 9952-197, 9952-198, 9952-199, 9952-200, 9952-201, 9952-202, 9952-203, 9952-204, 9952-205, 9952-206, 9952-207, 9952-208, 9952-209, 9952-210, 9952-211, 9952-212, 9952-213, 9952-214, 9952-215, 9952-216, 9952-217, 9952-218, 9952-219, 9952-220, 9952-221, 9952-222, 9952-223, 9952-224, 9952-225, 9952-226, 9952-227, 9952-228, 9952-229, 9952-230, 9952-231, 9952-232, 9952-233, 9952-234, 9952-235, 9952-236, 9952-237, 9952-238, 9952-239, 9952-240, 9952-241, 9952-242, 9952-243, 9952-244, 9952-245, 9952-246, 9952-247, 9952-248, 9952-249, 9952-250, 9952-251, 9952-252, 9952-253, 9952-254, 9952-255, 9952-256, 9952-257, 9952-258, 9952-259, 9952-260, 9952-261, 9952-262, 9952-263, 9952-264, 9952-265, 9952-266, 9952-267, 9952-268, 9952-269, 9952-270, 9952-271, 9952-272, 9952-273, 9952-274, 9952-275, 9952-276, 9952-277, 9952-278, 9952-279, 9952-280, 9952-281, 9952-282, 9952-283, 9952-284, 9952-285, 9952-286, 9952-287, 9952-288, 9952-289, 9952-290, 9952-291, 9952-292, 9952-293, 9952-294, 9952-295, 9952-296, 9952-297, 9952-298, 9952-299, 9952-300, 9952-301, 9952-302, 9952-303, 9952-304, 9952-305, 9952-306, 9952-307, 9952-308, 9952-309, 9952-310, 9952-311, 9952-312, 9952-313, 9952-314, 9952-315, 9952-316, 9952-317, 9952-318, 9952-319, 9952-320, 9952-321, 9952-322, 9952-323, 9952-324, 9952-325, 9952-326, 9952-327, 9952-328, 9952-329, 9952-330, 9952-331, 9952-332, 9952-333, 9952-334, 9952-335, 9952-336, 9952-337, 9952-338, 9952-339, 9952-340, 9952-341, and 9952-342, or pharmaceutical salts thereof. One of skill in the art will readily be able to identify the structure of the compound based on the compound numbers provided herein, in light of the teachings of the compound structures in the US 20040171073 application (see Table 1). In one embodiment, the compounds are one or more of 9952-53, 9952-61, 9952-19, 9952-29, and/or 9952-6, or pharmaceutical salts thereof.

Any suitable insulin secreting cell can be used, including but not limited to pancreatic β cells. As used herein, "pancreatic β cells" are any population of cells that contain pancreatic β islet cells. The cells can be obtained from any mammalian species, or may be present within the mammalian species when the assays are conducted in vivo. Such pancreatic β islet cell populations include the pancreas, isolated pancreatic islets of Langerhans ("pancreatic islets"), isolated pancreatic β islet cells, and insulin secreting cell lines. Methods for pancreatic isolation are well known in the art, and methods for isolating pancreatic islets, can be found, for example, in Cejvan et al., Diabetes 52:1176-1181 (2003); Zambre et al., Biochem. Pharmacol. 57:1159-1164 (1999), and Fagan et al., Surgery 124:254-259 (1998), and references cited therein. Insulin secreting cell lines are available from the American Tissue Culture Collection ("ATCC") (Rockville, Md.). In a further embodiment where pancreatic β cells are used, they are obtained from ob/ob mice, which contain more than 95% β cells in their islets, and are commercially available.

Measuring the density and/or conductivity of $Ca_v1$ channels can be carried out by standard methods in the art, including but not limited to single channel and whole-cell patch-clamp measurements (cell-attached and perforated whole-cell patch-clamp techniques). As used herein, "increase density and/or conductivity of $Ca_v1$ channels" refers to increasing during the course of the assay above that seen in the absence of test compounds. The method does not require a specific amount of increase in density and/or conductivity of $Ca_v1$ channels over baseline, so long as the compound(s) promotes an increase in density and/or conductivity of $Ca_v1$ channels above that seen in the absence of test compounds. In a preferred embodiment, the increase is a statistically significant increase as judged by standard statistical analysis.

The contacting of the first population of insulin-secreting cells with the apoCIII may occur before, after, or simultaneously with contacting the cells with one or more test compounds. Similarly, the contacting of the second population of insulin secreting cells with the SBIR inhibitor(s) may occur before, after, or simultaneously with contacting the cells with one or more test compounds. The contacting can be in vitro or in vivo (ex: in an experimental animal model). Any suitable culture conditions can be used for carrying out the methods of any of the candidate identification methods of the invention; preferably, the same experimental conditions are used in contacting the first and second population of cells with apoCIII and the one or more test compounds, with the only difference being the contacting of the second population of cells with the SBIR inhibitor(s). In one embodiment, the cells are contacted with ApoCIII for at least 6 hours. In another embodiment, the cells are grown in medium comprising between 1 mM and 15 mM glucose; preferably between 3 mM and 12 mM; preferably about 11 mM glucose. In a further embodiment, the cells are cultured at approximately 37° C. (preferably in a humidified incubator, such as 5% $CO_2$) prior to recording the density and/or conductivity of the $Ca_v1$ channels at approximately room temperature. Appropriate amounts of the one or more test compounds and the SBIR inhibitor(s) can be determined by one of skill in the art based on specifics of the particular assay to be used, in light of the teachings herein. These and other suitable assay conditions are well within the level of those of skill in the art, based on the teachings herein.

In one embodiment, the candidate compounds are candidate compounds for limiting development of and/or treating type 1 diabetes. In another embodiment, the candidate compounds are candidate compounds for limiting development of and/or treating type 2 diabetes. The present invention further provides compounds identified by the above screening methods, and their use for treating subjects in need thereof.

In another embodiment, the methods further comprise large-scale synthesis of the candidate compounds that inhibit apoCIII-induced increase in density and/or conductivity of $Ca_v1$ channels in the pancreatic β cells.

When the test compounds comprise polypeptide sequences, such polypeptides may be chemically synthesized or recombinantly expressed. Recombinant expression can be accomplished using standard methods in the art, as disclosed above. Such expression vectors can comprise bacterial or viral expression vectors, and such host cells can be prokaryotic or eukaryotic. Synthetic polypeptides, prepared using the well-known techniques of solid phase, liquid phase, or peptide condensation techniques, or any combination thereof, can include natural and unnatural amino acids. Amino acids used for peptide synthesis may be standard Boc (Nα-amino protected Nα-t-butyloxycarbonyl) amino acid resin with standard deprotecting, neutralization, coupling and wash protocols, or standard base-labile Nα-amino protected 9-fluorenylmethoxycarbonyl (Fmoc) amino acids. Both Fmoc and Boc Nα-amino protected amino acids can be obtained from Sigma, Cambridge Research Biochemical, or other chemical companies familiar to those skilled in the art. In addition, the polypeptides can be synthesized with other Nα-protecting groups that are familiar to those skilled in this art. Solid phase peptide synthesis may be accomplished by techniques familiar to those in the art and provided, such as by using automated synthesizers.

When the test compounds comprise antibodies, such antibodies can be polyclonal or monoclonal. The antibodies can be humanized, fully human, or murine forms of the antibodies. Such antibodies can be made by well-known methods, such as described in Harlow and Lane, Antibodies; A Laboratory Manual, Cold Spring Harbor Laboratory, Cold Spring Harbor, N.Y., (1988).

When the test compounds comprise nucleic acid sequences, such nucleic acids may be chemically synthesized or recombinantly expressed as well. Recombinant expression techniques are well known to those in the art (See, for example, Sambrook, et al., 1989, supra). The nucleic acids may be DNA or RNA, and may be single stranded or double. Similarly, such nucleic acids can be chemically or enzymatically synthesized by manual or automated reactions, using standard techniques in the art. If synthesized chemically or by in vitro enzymatic synthesis, the nucleic acid may be purified prior to introduction into the cell. For example, the nucleic acids can be purified from a mixture by extraction with a solvent or resin, precipitation, electrophoresis, chromatography, or a combination thereof. Alternatively, the nucleic acids may be used with no or a minimum of purification to avoid losses due to sample processing.

When the test compounds comprise compounds other than polypeptides, antibodies, or nucleic acids, such compounds can be made by any of the variety of methods in the art for conducting organic chemical synthesis.

In one embodiment, the method further comprises contacting a third population of insulin secreting cells with an amount of ApoCIII effective to increase density and/or conductivity of $Ca_v1$ channels, in the presence of one or more of the candidate compounds, and further contacting the third population of insulin secreting cells with a $Ca_v2$ and/or $Ca_v3$ channel blocker, wherein the candidate compounds that inhibit the ApoCIII-induced increase in density and/or conductivity in the third population of insulin secreting cells to a greater degree than in the first population of insulin secreting cells are preferred candidate compounds for limiting development of and/or treating diabetes. In this embodiment, the $Ca_v2$ and/or $Ca_v3$ channel blocker are selective for the $Ca_v2$ and/or $Ca_v3$ channel, and do not serve as a $Ca_v1$ channel blocker. Suitable $Ca_v2$ and/or $Ca_v3$ channel blockers include, but are not limited to, ω-agatoxin IVA, ω-conotoxin GVIA and SNX 482 ($Ca_v2$ channel blockers); and mibefradil and NNC 55-0396 ($Ca_v3$ channel blockers). It is within the level of those of skill in the art to determine, based on the teachings herein, the amount of any $Ca_v2$ and/or $Ca_v3$ channel blocker(s) that can be usefully used in a given assay.

In a further embodiment that can be combined with any of the embodiments herein, the method further comprises contacting a fourth population of insulin secreting cells with an amount of ApoCIII effective to increase density and/or conductivity of $Ca_v1$ channels, in the presence of one or more of the candidate compounds and further contacting the fourth population of insulin secreting cells with a Src kinase inhibitor and/or a protein kinase A (PKA) inhibitor, wherein those candidate compounds that inhibit the ApoCIII-induced increase in density and/or conductivity of $Ca_v1$ channels in the first population of insulin secreting cells to a greater degree than in fourth population of insulin secreting cells are preferred candidate compounds for limiting development of and/or treating diabetes.

As shown in the examples that follow, the inventors have discovered that ApoCIII hyperactivates β cell $Ca_v1$ channels through SRBI/β1 integrin-dependent co-activation of PKA and Src kinase. Thus, inhibitors of PKA and/or Src should down-regulate positive candidate compounds of the present invention. Therefore, those candidate compounds that inhibit the ApoCIII-induced increase in density and/or conductivity of $Ca_v1$ channels in the first population of insulin secreting cells to a greater degree than in fourth population of insulin secreting cells are preferred candidate compounds for limiting development of and/or treating diabetes. Any suitable PKA and/or Src kinase inhibitor can be used, including but not limited to those disclosed in the examples that follow. Exemplary Src kinase inhibitors include PP1 analogs, PP2, and compounds disclosed in the examples that follow. Exemplary PKA inhibitors include adenosine 3',5'-cyclic monophosphorothioate-R, H-7, H-8, H-9, H-89, and compounds disclosed in the examples that follow. It is within the level of those of skill in the art to determine, based on the teachings herein, the amount of any Src kinase inhibitor(s) and/or a PKA inhibitor(s) that can be usefully used in a given assay.

In another embodiment that can be combined with any of the embodiments herein, the methods further comprises contacting a fifth population of insulin secreting cells with an amount of ApoCIII effective to density and/or conductivity of $Ca_v1$ channels, in the presence of one or more of the candidate compounds, and further contacting the fifth population of insulin secreting cells with a molecule that inhibits β1 integrin expression or activity, wherein those positive test compounds that inhibit the ApoCIII-induced increase in density and/or conductivity of $Ca_v1$ channels in the first population of insulin secreting cells to a greater degree than in the fifth population of insulin secreting cells are preferred candidate compounds for limiting development of and/or treating diabetes.

As shown in the examples that follow, the inventors have discovered that ApoCIII hyperactivates β cell $Ca_v1$ channels through an SRBI-β1 integrin-dependent coactivation of PKA and Src kinase. Thus, inhibitors of β1 integrin should down-regulate positive candidate compounds of the present invention. Therefore, those candidate compounds that inhibit the ApoCIII-induced increase in density and/or conductivity of $Ca_v1$ channels in the first population of insulin secreting cells to a greater degree than in the fifth population of insulin secreting cells are preferred candidate compounds for limiting development of and/or treating diabetes. Any suitable β1 integrin inhibitor can be used (antibodies, antisense, siRNA, shRNA, etc.), including but not limited to those disclosed in the examples that follow. It is within the level of those of skill in the art to determine, based on the teachings herein, the amount of any β1 integrin inhibitor(s) that can be usefully used in a given assay.

In a second aspect, the present invention provides methods for identifying candidate compounds for limiting development of and/or treating diabetes, comprising (a) contacting a first population of insulin secreting cells with an amount of ApoCIII effective to increase density and/or conductivity of $Ca_v1$ channels, in the presence of one or more test compounds; and (b) identifying those positive test compounds that inhibit the ApoCIII-induced increase in density and/or conductivity of $Ca_v1$ channels and also inhibit SRBI expression or activity in the first population of insulin secreting cells compared to control, wherein the positive test compounds are candidate compounds for limiting development of and/or treating diabetes.

Methods for measuring the expression and/or activity of SRBI are known in the art. In non-limiting embodiments, RNA and/or protein expression can be monitored using standard reverse-transcription-polymerase chain reaction, Northern blotting, Western blotting, immunofluorescence, or other techniques. Activity of SRBI can be monitored using a variety of techniques, including but not limited to assaying for receptor blockade, as taught, for example, in J Pharm Pharmacol. 2006 December; 58(12):1629-38, incorporated by reference herein. It is well within the level of those of skill in the art to use other techniques for measuring SRBI expression and/or activity.

Any amount of SRBI expression and/or activity relative to control is considered "inhibition"; in various embodiments, the inhibition comprises at least 10%, 20%, 50%, 75%, 80%, 85%, 90%, 95%, 96%, 97%, 98%, 99%, or 100% of SRBI expression and/or activity compared to control.

In one embodiment, the control comprises contacting a second population of insulin secreting cells contacted with an amount of ApoCIII effective to increase density and/or conductivity of $Ca_v1$ channels, in the absence of one or more test compounds. This embodiment may comprise, for example, contacting the second population of cells with a formulation, such as a buffer, that is similar to or identical to the formulation the test compounds are dissolved in.

All embodiments of the first aspect of the invention can be used in this second aspect unless the context clearly dictates otherwise.

In one embodiment, the control comprises contacting a second population of insulin secreting cells contacted with ApoCIII in the absence of test compounds. This embodiment may comprise, for example, contacting the second population of cells with a formulation, such as a buffer, that is similar to or identical to the formulation the test compounds are dissolved in.

In a third aspect, the present invention provides methods for treating or limiting development of diabetes, comprising administering to a subject in need thereof with an amount effective of an inhibitor of SRBI expression and/or activity. In various embodiments, the inhibitor is selected from the group consisting of anti-SRBI antibodies, anti-SRBI aptamers, SRBI siRNAs, SRBI shRNAs, SRBI antisense oligonucleotides, and small molecules that inhibit SRBI expression and/or activity.

Any suitable molecule that inhibits SRBI expression or activity can be used in the therapeutic methods of the invention, including but not limited to anti-SRBI antibodies, anti-SRBI aptamers, SRBI siRNAs, SRBI shRNAs, SRBI antisense oligonucleotides, and small molecule SRBI inhibitors. Anti-SRBI antibodies are available from a variety of commercial suppliers, including ThermoFisher, Epitomics, and OriGene. In one embodiment, the inhibitor comprise interferon alpha, which has been shown to inhibit SRBI expression (Gut. 2008 May; 57(5):664-71. Epub 2007 Nov. 12). In another embodiment, the SRBI inhibitor comprises N-[4-(4-tert-Butoxycarbonylpiperazin-1-yl)phenyl]-(2-chloro-5-nitrophenyl)carboxamide (R-138329), which has been shown to block SRBI receptor activity (J Pharm Pharmacol. 2006 December; 58(12):1629-38). In another embodiment, the SRBI inhibitor comprises 2-Hexyl-1-cyclopentanone thiosemicarbazone, 33M20, BLT1, Block lipid transport-1, CAS Number 321673-30-7 (Available from Sigma Aldrich). In another embodiment, the SRBI inhibitor is any one or more of the SRBI inhibitors disclosed in US 20040171073 (incorporated by reference herein in its entirety), and identified as MIT 9952-1, 9952-2, 9952-3, 9952-4, 9952-5, 9952-6, 9952-7, 9952-8, 9952-9, 9952-10, 9952-11, 9952-12, 9952-13, 9952-14, 9952-15, 9952-16, 9952-17, 9952-18, 9952-19, 9952-20, 9952-21, 9952-22, 9952-23, 9952-24, 9952-25, 9952-26, 9952-27, 9952-28, 9952-29, 9952-30, 9952-31, 9952-32, 9952-33, 9952-34, 9952-35, 9952-36, 9952-37, 9952-38, 9952-39, 9952-40, 9952-41, 9952-42, 9952-43, 9952-44, 9952-45, 9952-46, 9952-47, 9952-48, 9952-49, 9952-50, 9952-51, 9952-52, 9952-53, 9952-54, 9952-55, 9952-56, 9952-57, 9952-58, 9952-59, 9952-60, 9952-61, 9952-62, 9952-63, 9952-64, 9952-65, 9952-66, 9952-67, 9952-68, 9952-69, 9952-70, 9952-71, 9952-72, 9952-73, 9952-74, 9952-75, 9952-76, 9952-77, 9952-78, 9952-79, 9952-80, 9952-81, 9952-82, 9952-83, 9952-84, 9952-85, 9952-86, 9952-87, 9952-88, 9952-89, 9952-90, 9952-91, 9952-92, 9952-93, 9952-94, 9952-95, 9952-96, 9952-97, 9952-98, 9952-99, 9952-100, 9952-101, 9952-102, 9952-103, 9952-104, 9952-105, 9952-106, 9952-107, 9952-108, 9952-109, 9952-110, 9952-111, 9952-112, 9952-113, 9952-114, 9952-115, 9952-116, 9952-117, 9952-118, 9952-119, 9952-120, 9952-121, 9952-122, 9952-123, 9952-124, 9952-125, 9952-126, 9952-127, 9952-128, 9952-129, 9952-130, 9952-131, 9952-132, 9952-133, 9952-134, 9952-135, 9952-136, 9952-137, 9952-138, 9952-139, 9952-140, 9952-141, 9952-142, 9952-143, 9952-144, 9952-145, 9952-146, 9952-147, 9952-148, 9952-149, 9952-150, 9952-151, 9952-152, 9952-153, 9952-154, 9952-155, 9952-156, 9952-157, 9952-158, 9952-159, 9952-160, 9952-161, 9952-162, 9952-163, 9952-164, 9952-165, 9952-166, 9952-167, 9952-168, 9952-169, 9952-170, 9952-171, 9952-172, 9952-173, 9952-174, 9952-175, 9952-176, 9952-177, 9952-178, 9952-179, 9952-180, 9952-181, 9952-182, 9952-183, 9952-184, 9952-185, 9952-186, 9952-187, 9952-188, 9952-189, 9952-190, 9952-191, 9952-192, 9952-193, 9952-194, 9952-195, 9952-196, 9952-197, 9952-198, 9952-199, 9952-200, 9952-201, 9952-202, 9952-203, 9952-204, 9952-205, 9952-206, 9952-207, 9952-208, 9952-209, 9952-210, 9952-211, 9952-212, 9952-213, 9952-214, 9952-215, 9952-216, 9952-217, 9952-218, 9952-219, 9952-220, 9952-221, 9952-222, 9952-223, 9952-224, 9952-225, 9952-226, 9952-227, 9952-228, 9952-229, 9952-230, 9952-231, 9952-232, 9952-233, 9952-234, 9952-235, 9952-236, 9952-237, 9952-238, 9952-239, 9952-240, 9952-241, 9952-242, 9952-243, 9952-244, 9952-245, 9952-246, 9952-247, 9952-248, 9952-249, 9952-250, 9952-251, 9952-252, 9952-253, 9952-254, 9952-255, 9952-256, 9952-257, 9952-258, 9952-259, 9952-260, 9952-261, 9952-262, 9952-263, 9952-264, 9952-265, 9952-266, 9952-267, 9952-268, 9952-269, 9952-270, 9952-271, 9952-272, 9952-273, 9952-274, 9952-275, 9952-276, 9952-277, 9952-278, 9952-279, 9952-280, 9952-281, 9952-282, 9952-283, 9952-284, 9952-285, 9952-286, 9952-287, 9952-288, 9952-289, 9952-290, 9952-291, 9952-292, 9952-293, 9952-294, 9952-295, 9952-296, 9952-297, 9952-298, 9952-299, 9952-300, 9952-301, 9952-302, 9952-303, 9952-304, 9952-305, 9952-306, 9952-307, 9952-308, 9952-309, 9952-310, 9952-311, 9952-312, 9952-313, 9952-314, 9952-315, 9952-316, 9952-317, 9952-318, 9952-319, 9952-320, 9952-321, 9952-322, 9952-323, 9952-324, 9952-325, 9952-326, 9952-327, 9952-328, 9952-329, 9952-330, 9952-331, 9952-332, 9952-333, 9952-334, 9952-335, 9952-336, 9952-337, 9952-338, 9952-339, 9952-340, 9952-341, and 9952-342, or salts thereof. In one embodiment, the compounds are one or more of 9952-53, 9952-61, 9952-19, 9952-29, and/or 9952-6, or pharmaceutical salts thereof.

In one embodiment of this third aspect, the methods further comprise administering amount effective of an inhibitor of PKA and Src kinase to treat or limit development of diabetes. Exemplary Src kinase inhibitors include PP1 analogs, PP2, and compounds disclosed in the examples that follow. Exemplary PKA inhibitors include adenosine 3',5'-cyclic monophosphorothioate-R, H-7, H-8, H-9, H-89, and compounds disclosed in the examples that follow.

In another embodiment of this third aspect, the methods further comprise administering an amount effective of an inhibitor of β1 integrin expression and/or activity. In various embodiments, the inhibitor is selected from the group consisting of an anti-β1 integrin antibody, anti-β1 integrin aptamer, β1 integrin siRNA, β1 integrin shRNA, and β1 integrin antisense oligonucleotides.

In a further embodiment of this third aspect, the methods further comprise administering an amount effective of an inhibitor of ApoCIII activation of pancreatic β cells. As used herein, an "inhibitor" of apoCIII activation includes compounds that reduce the transcription of apoCIII DNA into RNA, compounds that reduce translation of the apoCIII RNA into protein, and compounds that reduce the function of apoCIII protein. Such inhibiting can be complete inhibition or partial inhibition, such that the expression and/or activity of the apoCIII is reduced, resulting in a reduced ability to increase intracellular calcium concentration. Such inhibitors are selected from the group consisting of antibodies that bind to apoCIII; aptamers that can interfere with apoCIII activity; antisense oligonucleotides directed against the apoCIII protein, DNA, or mRNA; small interfering RNAs (siRNAs) or short hairpin RNAs (shRNAs) directed against the apoCIII protein, DNA, or mRNA, and any other chemical or biological compound that can interfere with apoCIII activity.

In one embodiment of each of these therapeutic aspects, the method is for treating diabetes. In this embodiment, the subject has been diagnosed with type 1 or type 2 diabetes. As used herein, "diabetes" is characterized by insufficient or no production of insulin by the pancreas, leading to high blood sugar levels.

As used herein, "treating diabetes" means accomplishing one or more of the following: (a) reducing the severity of the diabetes or diabetic complications; (b) limiting or preventing development of diabetic complications; (c) inhibiting worsening of diabetic complications or of symptoms characteristic of diabetes; (d) limiting or preventing recurrence diabetic complications or of symptoms characteristic of diabetes; (e) limiting or preventing recurrence of diabetic complications or of symptoms characteristic of diabetes in patients that were previously symptomatic.

Symptoms characteristic of diabetes include, but are not limited to, elevated blood glucose levels, decreased insulin production, insulin resistance, proteinuria, and impaired glomerular clearance. Diabetic complications that can be treated according to the methods of the invention include, but are not limited to, complications in the nerves (such as diabetic neuropathy) and complications associated with smooth muscle cell dysregulaton (including but not limited to erectile dysfunction, bladder dysfunction, and vascular complications including but not limited to atherosclerosis, stroke, and peripheral vascular disease)

In another embodiment, the method is for limiting development of diabetes. In this aspect, the subject is at risk of type 1 or type 2 diabetes, and a benefit is to limit development of diabetes and/or diabetic complications. Any subject at risk of developing diabetes can be treated, including but not limited to subjects with one or more of, metabolic syndrome, known genetic risk factors for diabetes, a family history of diabetes, and obesity.

In a further embodiment, the methods for treating or limiting development of diabetes and/or diabetic complications further comprises treating those individuals that have been identified as overexpressing apoCIII compared to control. Increases in apoCIII expression precede development of diabetic complications, and thus this embodiment permits early detection of suitable patients for treatment using the methods of the invention.

As used herein, "overexpression" is any amount of apoCIII expression above control. Any suitable control can be used, including apoCIII expression levels from a subject known not to be suffering from diabetes, or previously determined standardized expression levels of apoCIII from a population of similar patient samples. Any amount of increased apoCIII expression relative to control is considered "overexpression"; in various embodiments, the overexpression comprises at least 10%, 20%, 50%, 100%, 200%, or greater increased apoCIII expression compared to control. In a preferred embodiment, apoCIII expression is detected in blood or serum samples. In one embodiment to evaluate the levels of apoCIII in sera, albumin is removed from serum samples using standard techniques, such as via use of Montage Albumin Deplete Kit (Millipore) or AlbuSorb™ (Biotech Support Group). The collected sera samples can then be freeze-dried overnight and run on sep-Pak C18. The eluted proteins can be freeze-dried and thereafter dissolved in 100 µL 0.1% TFA and run on an ACE C18 10-×0.21-cm column 20-60%, and the area under the curve, where apoCIII elutes, evaluated. ApoCIII can be identified using any suitable technique, including but not limited to MALDI mass spectrometry.

As used herein, the term "subject" or "patient" is meant any subject for which therapy is desired, including humans, cattle, dogs, cats, guinea pigs, rabbits, rats, mice, insects, horses, chickens, and so on. Most preferably, the subject is human.

The therapeutic may be administered by any suitable route, including but not limited to oral, topical, parenteral, intranasal, pulmonary, or rectal in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a compound of the invention and a pharmaceutically acceptable carrier. The therapeutic may be present in association with one or more non-toxic pharmaceutically acceptable carriers and/or diluents and/or adjuvants, and if desired other active ingredients. The therapeutic may be in a form suitable for oral use, for example, as tablets, troches, lozenges, aqueous or oily suspensions, dispersible powders or granules, emulsion, hard or soft capsules, or syrups or elixirs.

The therapeutic may be combined with a pharmaceutically acceptable carrier. Suitable acids which are capable of forming such salts include inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid and the like. Suitable bases capable of forming such salts include inorganic bases such as sodium hydroxide, ammonium hydroxide, potassium hydroxide and the like; and organic bases such as mono-, di- and tri-alkyl and aryl amines (e.g., triethylamine, diisopropyl amine, methyl amine, dimethyl amine and the like) and optionally substituted ethanolamines (e.g., ethanolamine, diethanolamine and the like).

The dosage range depends on the choice of the compound, the route of administration, the nature of the formulation, the nature of the subject's condition, and the judgment of the attending practitioner. For example, oral administration would be expected to require higher dosages than administration by intravenous injection. Variations in these dosage levels can be adjusted using standard empirical routines for optimization, as is well understood in the art Example 1

Apolipoprotein CIII Hyperactivates β Cell $Ca_V1$ Channels through SRBI/β1 Integrin-Dependent Coactivation of PKA and Src Summary Apolipoprotein CIII (ApoCIII) not only serves as an inhibitor of triglyceride hydrolysis, but also participates in diabetes-related pathological events such as hyperactivation of voltage-gated $Ca^{2+}$ ($Ca_V$) channels in the pancreatic β cell. However, nothing is known about the molecular mechanisms whereby ApoCIII hyperactivates β cell $Ca_V$ channels. We now demonstrate that ApoCIII increased $Ca_V1$ channel open probability and density. ApoCIII enhanced whole-cell $Ca^{2+}$ currents and the $Ca_V1$ channel blocker nimodipine completely abrogated this enhancement. The effect of ApoCIII was not influenced by individual inhibition of PKA, PKC or Src. However, combined inhibition of PKA, PKC and Src counteracted the effect of ApoCIII, similar results obtained by coinhibition of PKA and Src. Moreover, knockdown of β1 integrin or scavenger receptor class B type I (SRBI) prevented ApoCIII from hyperactivating β cell $Ca_V$ channels. These data reveal that ApoCIII hyperactivates β cell $Ca_V1$ channels through SRBI/β1 integrin-dependent coactivation of PKA and Src.

Results

Apolipoprotein CIII Increases $Ca_V1$ Channel Density and Conductivity in the β Cell.

Our previous work reveals that ApoCIII incubation significantly enhances whole-cell $Ca^{2+}$ currents in the mouse islet β cell[5]. To clarify what type of β cell $Ca_V$ channels and whether the density or conductivity was affected, we analyzed unitary $Ca_V1$ channel currents, characterized by a large unitary $Ba^{2+}$ conductance with long-lasting openings, in mouse islet β cells (FIG. 1a) and RINm5F cells (FIG. 1c), following ApoCIII incubation. In experiments with mouse islet β cells, we observed more $Ca_V1$ channels, reflected by more layers of unitary $Ba^{2+}$ currents, in plasma membrane patches of ApoCIII-treated cells than in those of control cells (FIG. 1a). The average number, open probability and mean open time of unitary $Ca_V1$ channels in ApoCIII-treated cells (n=32) were significantly greater than those in cells exposed to control vehicle (n=33) (FIG. 1b). The mean closed time of unitary $Ca_V1$ channels recorded in patches of ApoCIII-incubated cells was significantly shorter than that in control patches (FIG. 1b). Likewise, similar effects of ApoCIII occurred on $Ca_V1$ channels in insulin-secreting RINm5F cells. Plasma membrane patches of ApoCIII-incubated cells accommodated more $Ca_V1$ channels in comparison with those of vehicle-treated cells (FIG. 1c). $Ca_V1$ channels in the former opened more frequently than those in the latter (FIG. 1c). ApoCIII incubation (n=35) significantly increased channel number, elevated open probability, prolonged mean open time and shortened mean closed time of $Ca_V1$ channels as compared with incubation with vehicle solution (n=34) (FIG. 1d). Obviously, the data reveal that ApoCIII increased both density and conductivity of β cell $Ca_V1$ channels.

Pharmacological Ablation of $Ca_V1$ Channels Prevents Apolipoprotein CIII-Induced Hyperactivation of β Cell $Ca_V$ Channels.

Figure 2:
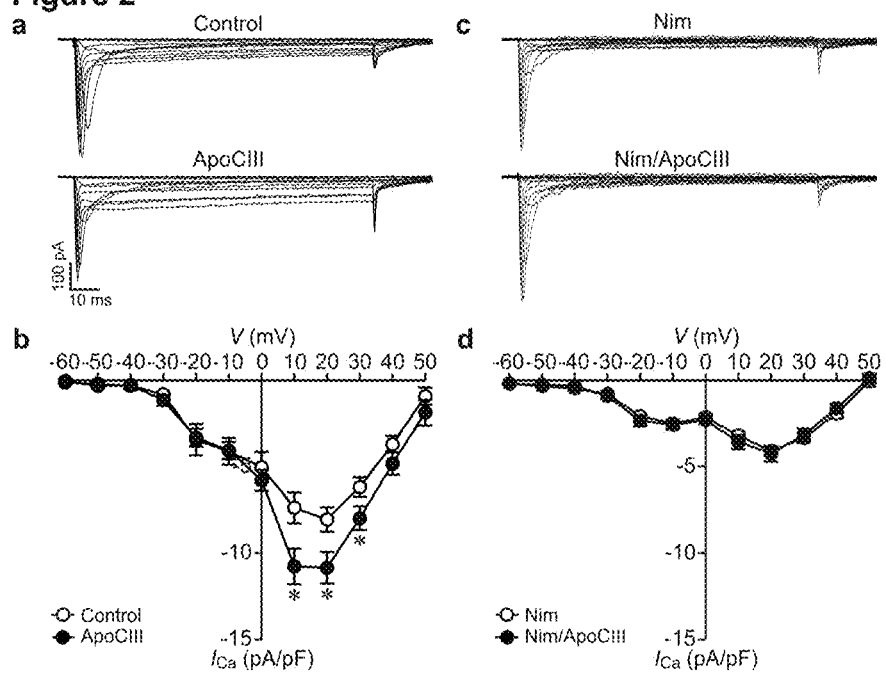
FIG. 2. Apolipoprotein CIII incubation increases whole-cell $Ca^{2+}$ currents and coincubation with the $Ca_V1$ channel blocker nimodipine abrogates the effect of apolipoprotein CIII incubation in RINm5F cells. (a) Sample whole-cell $Ca^{2+}$ current traces from a cell incubated with vehicle solution as control (cell capacitance: 10.1 pF) and apolipoprotein CIII (ApoCIII)-treated cell (cell capacitance: 11.1 pF). (b) Average $Ca^{2+}$ current density-voltage relationships in control cells (open circles, n=26) and cells treated with ApoCIII (filled circles, n=26). *$P<0.05$ and **$P<0.01$ versus control. (c) Sample whole-cell $Ca^{2+}$ current traces from a nimodipine (Nim)-incubated cell (cell capacitance: 10 pF) and a cell exposed to Nim together with ApoCIII (Nim/ApoCIII) (cell capacitance: 11.9 pF). (d) Average $Ca^{2+}$ current density-voltage relationships in Nim-treated cells (open circles, n=20) and cells incubated with Nim/ApoCIII (filled circles, n=21). *$P<0.05$ and **$P<0.01$ versus Nim alone.

The verification of the effects of ApoCIII on $Ca_V1$ channels by single channel analysis does not necessarily mean that ApoCIII only attacks $Ca_V1$ channels. To examine if the effects also occur on other types of $Ca_V$ channels, we analyzed whole-cell $Ca^{2+}$ currents in RINm5F cells following ApoCIII incubation in the absence and presence of the $Ca_V1$ channel blocker nimodipine. Whole-cell $Ca^{2+}$ currents in cells incubated with ApoCIII were larger than those in cells treated with vehicle solution (FIG. 2a). Whole-cell $Ca^{2+}$ current densities observed in the voltage range from 10 to 30 mV in the ApoCIII group were significantly higher than those in the control group (FIG. 2b). In striking contrast, whole-cell $Ca^{2+}$ currents were similar between control cells and cells incubated with ApoCIII in the presence of nimodipine (FIG. 2c). There was no significant difference in the whole-cell $Ca^{2+}$ current density between the two treatments (FIG. 2d). The data confirm that ApoCIII solely impinge on β cell $Ca_V1$ channels.

Apolipoprotein CIII Hyperactivates β Cell $Ca_V$ Channels Via Coactivation of PKA and Src Kinase.

The increase in open probability of β cell $Ca_V1$ channels by ApoCIII and the mediating role of protein kinases in ApoCIII signaling suggest that ApoCIII may signal upstream of some protein kinases to hyperactivate β cell $Ca_V$ channels[16,19-22]. Therefore, we explored the involvement of PKA, PKC and Src kinase in ApoCIII-induced hyperactivation of β cell $Ca_V$ channels.

Figure 3:
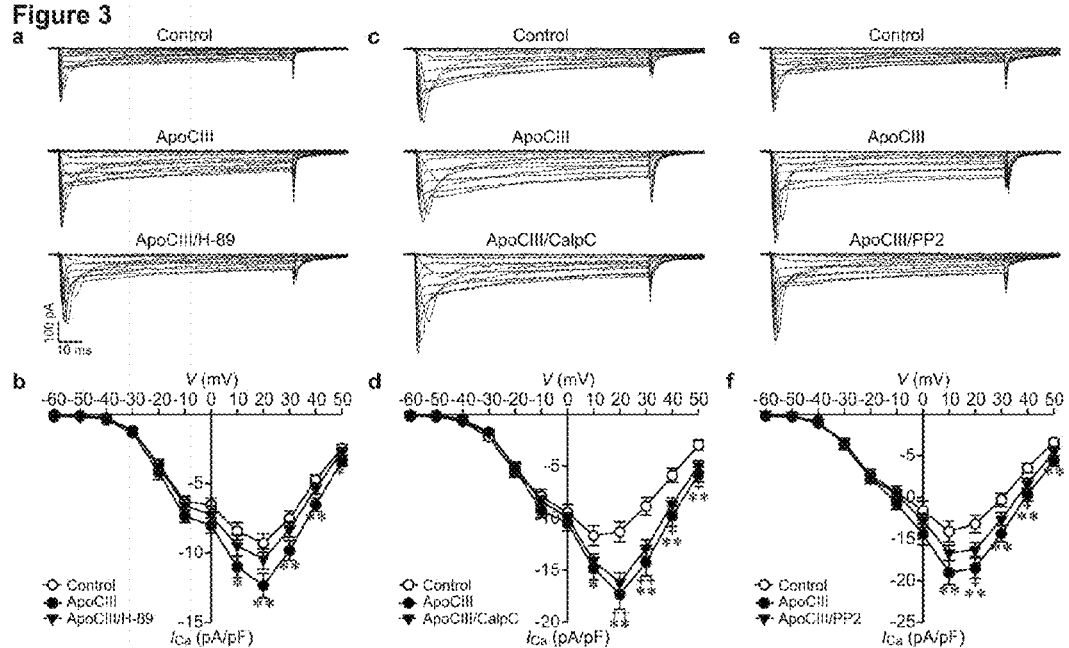
FIG. 3. PKA or Src kinase inhibition marginally reduces, but PKC inhibition does not affect apolipoprotein CIII-induced enhancement of whole-cell $Ca^{2+}$ currents in RINm5F cells. (a) Sample whole-cell $Ca^{2+}$ current traces from a cell incubated with vehicle solution as control (cell capacitance: 8.5 pF), an apolipoprotein CIII (ApoCIII)-treated cell (cell capacitance: 8.2 pF) and a cell exposed to ApoCIII plus the PKA inhibitor H-89 (ApoCIII/H-89, cell capacitance: 8.4 pF). (b) Average $Ca^{2+}$ current density-voltage relationships in control cells (open circles, n=37) and cells treated with ApoCIII (filled circles, n=36) or ApoCIII/H-89 (filled triangles, n=36). *$P<0.05$ and **$P<0.01$ versus control. (c) Sample whole-cell $Ca^{2+}$ current traces registered in a control cell (cell capacitance: 12.5 pF), an ApoCIII-incubated cell (cell capacitance: 12.0 pF) and a cell subjected to cotreatment with ApoCIII and the PKC inhibitor calphostin C (ApoCIII/CalpC, cell capacitance: 12.1 pF). (d) Average $Ca^{2+}$ current density-voltage relationships in control cells (open circles, n=33), ApoCIII-treated cells (filled circles, n=33) and cells exposed to ApoCIII/CalpC (filled triangles, n=33). *$P<0.05$ and $P<0.01$ ApoCIII versus control. +$P<0.05$ and ++$P<0.01$ ApoCIII/CalpC versus control. (e) Sample whole-cell $Ca^{2+}$ current traces acquired in a control cell (cell capacitance: 9.5 pF), an ApoCIII-incubated cell (cell capacitance: 9.2 pF) and a cell exposed to ApoCIII together with the Src kinase inhibitor PP2 (ApoCIII/PP2, cell capacitance: 10.0 pF). (f) Average $Ca^{2+}$ current density-voltage relationships in control cells (open circles, n=40) and cells incubated with ApoCIII (filled circles, n=40) or ApoCIII/PP2 (filled triangles, n=40). $P<0.01$ ApoCIII versus control. +$P<0.05$ ApoCIII/PP2 versus control.

First, we examined the effect of the PKA inhibitor H-89 on ApoCIII-induced hyperactivation of β cell $Ca_V$ channels in RINm5F cells. Whole-cell $Ca^{2+}$ currents registered in control cells were larger than those in cells treated with ApoCIII, whereas whole-cell $Ca^{2+}$ currents recorded in cells incubated with ApoCIII plus H-89 sized in between (FIG. 3a). Average $Ca^{2+}$ current densities measured in ApoCIII-treated cells (filled circles, n=36) were significantly higher than those in vehicle-treated control cells (open circles, n=37) at voltages ranging from 10 to 50 mV (FIG. 3b). However, cells following cotreatment of ApoCIII and H-89 (filled triangles, n=36) did not significantly differ from either cells treated with ApoCIII or control cells in terms of $Ca^{2+}$ current density (FIG. 3b). Moreover, H-89 treatment did not significantly influence $Ca^{2+}$ current densities under basal conditions, i.e. in the absence of ApoCIII (FIG. 8a,b). The results indicate that PKA inhibition marginally reduced ApoCIII-induced hyperactivation of β cell $Ca_V$ channels.

Second, we tested the effect of the PKC inhibitor calphostin C (CalpC) on ApoCIII-induced hyperactivation of β cell $Ca_V$ channels in RINm5F cells. We observed that cells incubated with ApoCIII and ApoCIII/CalpC-cotreated cells displayed similar whole-cell $Ca^{2+}$ currents, which were larger than those acquired in vehicle-treated cells (FIG. 3c). Mean $Ca^{2+}$ current densities in ApoCIII-treated cells (filled circles, n=33) at the voltage range 10-50 mV and cells exposed to ApoCIII/CalpC (filled triangles, n=33) at a voltage range from 20 to 50 mV increased significantly in comparison with vehicle-treated control cells (open circles, n=33) (FIG. 3d). There is no difference between ApoCIII-treated cells and ApoCIII/CalpC-cotreated cells with regard to the $Ca^{2+}$ current density (FIG. 3d). Furthermore, cells exposed to control vehicle were similar to CalpC-treated cells in terms of $Ca^{2+}$ current density (FIG. 8c,d). These data demonstrate that PKC inhibition does not affect ApoCIII-induced hyperactivation of β cell $Ca_V$ channels.

Third, we evaluated the effect of the Src kinase inhibitor PP2 on ApoCIII-induced hyperactivation of β cell $Ca_V$ channels in RINm5F cells. We found smaller and larger whole-cell $Ca^{2+}$ currents in cells following incubation with vehicle solution and ApoCIII-incubated cells, respectively (FIG. 3e). Cells exposed to ApoCIII and PP2 fell between vehicle control cells and cells treated with ApoCIII with regard to whole-cell $Ca^{2+}$ currents (FIG. 3e). Whole-cell $Ca^{2+}$ current densities quantified in cells treated with ApoCIII (filled circles, n=40) at the voltage range 10-50 mV were significantly elevated as compared with those determined in vehicle control cells (open circles, n=40) (FIG. 3f). Cells subjected to cotreatment of ApoCIII and PP2 (filled triangles, n=40) showed significantly larger $Ca^{2+}$ currents at the voltage range 20-40 mV compared to vehicle-treated control cells (open circles, n=40). However, the difference in the $Ca^{2+}$ current density between ApoCIII/PP2-cotreated cells and cells incubated with vehicle solution is less prominent than that between cells treated with ApoCIII and vehicle-treated control cells (FIG. 3f). Moreover, vehicle-treated cells (open circles, n=20) and cells incubated with PP2 (filled circles, n=19) exhibited similar $Ca^{2+}$ current densities (FIG. 8e,f). The results suggest that Src kinase inhibition has a tendency to decrease ApoCIII-induced hyperactivation of β cell $Ca_V$ channels.

Figure 4:
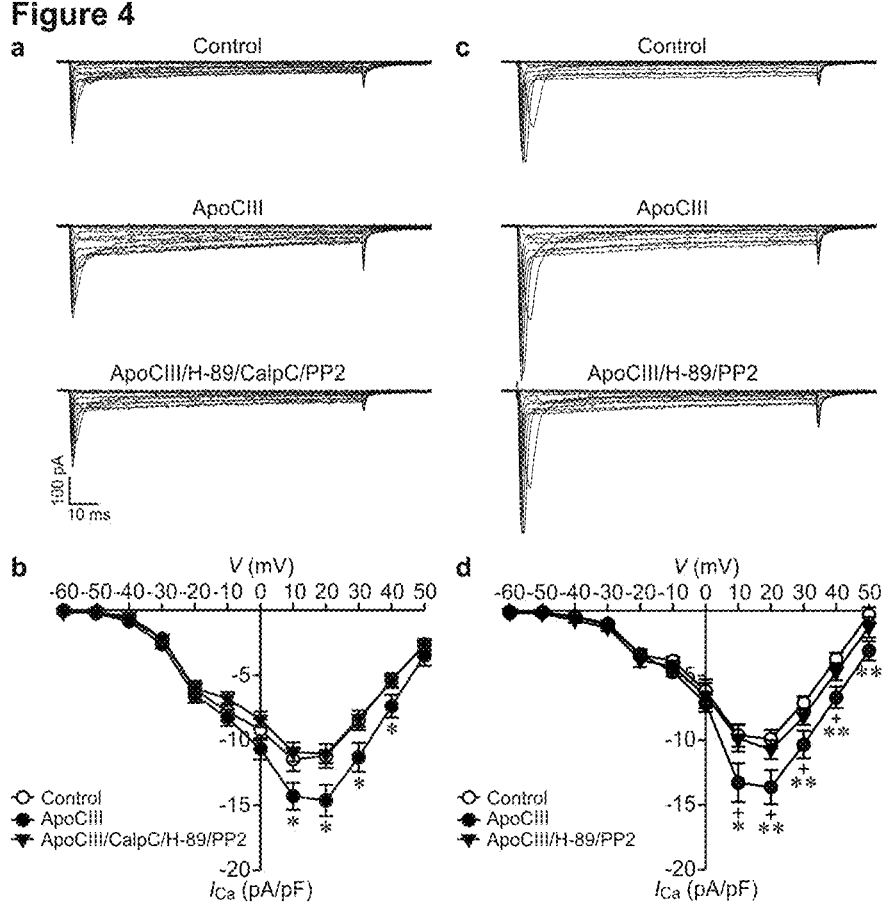
FIG. 4. Combined inhibition of PKA, PKC and Src kinase counteracts apolipoprotein CIII-induced augmentation of whole-cell $Ca^{2+}$ currents in RINm5F cells and coinhibition of PKA and Src kinase is sufficient to obtain this counteraction. (a) Sample whole-cell $Ca^{2+}$ current traces registered in a vehicle-incubated cell (Control, cell capacitance: 7.9 pF), a cell subsequent to apolipoprotein (ApoCIII) treatment (cell capacitance: 7.0 pF) and a cell exposed to ApoCIII in the presence of the protein kinase inhibitor cocktail of H-89, calphostin C and PP2 (ApoCIII/H-89/CalpC/PP2, cell capacitance: 7.2 pF). (b) Average $Ca^{2+}$ current density-voltage relationships in control cells (n=35) and cells exposed to ApoCIII (n=34) or to ApoCIII/H-89/CalpC/PP2 (n=35). *$P<0.05$ versus control and apoCIII/H-89/CalpC/PP2. (c) Sample whole-cell $Ca^{2+}$ current traces from a control cell (cell capacitance: 8.5 pF), a cell subsequent to ApoCIII treatment (cell capacitance: 8.2 pF) and a cell exposed to ApoCIII in the presence of the protein kinase inhibitors H-89 and PP2 (ApoCIII/H-89/PP2, cell capacitance: 8.7 pF). (d) Average $Ca^{2+}$ current density-voltage relationships in control cells (n=26) and cells subjected to ApoCIII (n=26) or to ApoCIII/H-89/PP2 (n=27). *$P<0.05$ and **$P<0.01$ versus control; +$P<0.05$ versus ApoCIII/H-89/PP2.

The marginal and null effects of PKA, PKC or Src kinase inhibitors on ApoCIII-induced hyperactivation of β cell $Ca_V$ channels made us wonder what happens if a more complex inhibition of all these kinases is applied. To address this question, we characterized the effect of the protein kinase inhibitor cocktail H-89, CalpC and PP2 on ApoCIII-induced hyperactivation of β cell $Ca_V$ channels in RINm5F cells. Larger whole-cell $Ca^{2+}$ currents appeared in an ApoCIII-treated cells, whereas smaller whole-cell $Ca^{2+}$ currents occurred in vehicle-treated control cells and cells treated with ApoCIII in the presence of H-89, CalpC and PP2 (FIG. 4a). ApoCIII treatment (filled circles, n=35) significantly increased $Ca^{2+}$ current densities at the voltage range 10-50 mV as compared with vehicle-treated control cells (open circles, n=35) and treatment with ApoCIII together with H-89, CalpC and PP2 (filled triangles, n=34). The profile of $Ca^{2+}$ current densities in cells exposed to ApoCIII in the presence of H-89, CalpC and PP2 resembled that in vehicle-treated control cells (FIG. 4b). Furthermore, treatment of control cells with the protein kinase inhibitor cocktail H-89, CalpC and PP2 had no significant effect on whole-cell $Ca^{2+}$ currents under basal conditions, i.e. in the absence of ApoCIII (FIG. 9a,b). The results demonstrate that combined inhibition of PKA, PKC and Src kinase effectively ablates ApoCIII-induced hyperactivation of β cell $Ca_V$ channels.

The marginal effect of PKA or Src kinase inhibitors alone on whole-cell $Ca^{2+}$ currents inevitably raised the question if coinhibition of PKA and Src kinase is sufficient to prevent ApoCIII-induced hyperactivation of β cell $Ca_V$ channels. We answered the question by analyzing whole-cell $Ca^{2+}$ currents in RINm5F cells following cotreatment with H-89 and PP2. We observed that whole-cell $Ca^{2+}$ currents in ApoCIII-treated cells were larger than those in control cells or cells subjected to treatment with ApoCIII in the presence of H-89 and PP2 (FIG. 4c). Significantly higher densities of whole-cell $Ca^{2+}$ currents appeared in the ApoCIII group (filled circles, n=26) in comparison with control group (open circles, n=26) or the group subjected to incubation with ApoCIII in the presence of H-89 and PP2 (filled triangles, n=27) (FIG. 4d). Moreover, whole-cell $Ca^{2+}$ currents in control cells resembled those observed in cells treated with H-89 and PP2 (FIG. 9c,d). These data reveal that ApoCIII enhances whole-cell $Ca^{2+}$ currents via coactivation of PKA and Src Kinase.

Apolipoprotein CIII does not Influence β Cell $Ca_V1$ Channel Expression.

Overnight incubation with ApoCIII may influence β cell $Ca_V1$ channel expression. To test for this possibility, we analyzed β cell $Ca_V1$ channel expression in RINm5F cells following ApoCIII incubation. We found that anti-$Ca_V1.2$, anti-$Ca_V1.3$ and anti-GAPDH antibodies detected clear $Ca_V1.2$, $Ca_V1.3$ and GAPDH immunoreactive bands, respectively. Control and ApoCIII-treated samples gave similar intensities of $Ca_V1.2$, $Ca_V1.3$ and GAPDH immunoreactivities (FIG. 5a). FIG. 5b shows that there was no significant difference in the relative abundance of $Ca_V1.2$ (hatched column, n=6) and $Ca_V1.3$ subunits (filled column, n=6) in RINm5F cell homogenates subjected to ApoCIII incubation in comparison with vehicle incubation (open column, n=6) (P>0.05). The data reveal that ApoCIII incubation did not alter β cell $Ca_V1$ channel expression at the protein level.

Apolipoprotein CIII Upregulates β Cell $Ca_V$ Channels Via β1 Integrin.

β1 integrin has been verified to serve as a mediator between ApoCIII and a certain number of protein kinases including PKA and Src kinase[16,19-22]. This together with our results that ApoCIII hyperactivated β cell $Ca_V$ channels via coactivation of PKA and Src kinase raise the possibility that β1 integrin mediates ApoCIII-induced hyperactivation of β cell $Ca_V$ channels. We investigated this possibility by implementing RNA interference in combination with whole-cell $Ca^{2+}$ current analysis in RINm5F cells. It turned out that transfection with two β1 integrin siRNAs significantly decreased β1 integrin expression at the protein level (FIG. 6a,b). Importantly, β1 integrin siRNA pretransfection effectively prevented ApoCIII-induced hyperactivation of β cell $Ca_V$ channels (FIG. 6c,d). Whole-cell $Ca^{2+}$ currents in β1 integrin siRNA-pretransfected cells incubated with ApoCIII (β1 integrin siRNA/ApoCIII) were significantly smaller than those in negative control siRNA-pretransfected cells exposed to ApoCIII (NC siRNA/apoCIII), but similar to those in three sets of control cells (FIG. 6c). These control cells were subjected to mock (NO siRNA/Control), negative control siRNA (NC siRNA/Control) and β1 integrin siRNA pretransfection (β1 integrin siRNA/Control), respectively, followed by control vehicle incubation (FIG. 6c). Significantly-reduced $Ca^{2+}$ current density was observed in cells subsequent to β1 integrin siRNA/ApoCIII (n=29) in comparison with those to NC siRNA/apoCIII (filled triangles, n=28) (FIG. 6d). The former displayed similar $Ca^{2+}$ current density, but the latter exhibited larger $Ca^{2+}$ current density compared with those subjected to NO siRNA/Control (n=29), NC siRNA/Control (n=28) or β1 integrin siRNA/Control (n=29) (FIG. 6d). Taken together, the results demonstrate that ApoCIII critically relies on β1 integrin to hyperactivate β cell $Ca_V$ channels.

Apolipoprotein CIII Hyperactivates β Cell $Ca_V$ Channels Via SRBI.

Previous studies have shown that there is no direct interaction of ApoCIII with β1 integrin[16,18]. In search for a molecular bridge between ApoCIII and β1 integrin we focused our interest to SRBI since this receptor physically associates with ApoCIII and interacts with β1 integrin[10,23]. We combined siRNA-mediated gene silencing and whole-cell $Ca^{2+}$ current analysis to examine if SRBI can serve as a molecular bridge between ApoCIII and β1 integrin in hyperactivating β cell $Ca_V1$ channels. As shown in FIG. 7a,b,c,d, SRBI siRNA transfection significantly lowered SRBI at both mRNA and protein levels in RINm5F cells. It is important to note that such downregulation sufficiently abolished enhancement of whole-cell $Ca^{2+}$ currents by ApoCIII (FIG. 7e,f). FIG. 7e shows that SRBI siRNA pretransfected cells incubated with ApoCIII (SRBI siRNA/ApoCIII) exhibited smaller whole-cell $Ca^{2+}$ currents as compared with those pretransfected with negative control siRNA followed by ApoCIII exposure (NC siRNA/apoCIII). Whole-cell $Ca^{2+}$ currents in cells subjected to SRBI siRNA/ApoCIII did not differ from those in control vehicle-treated cells subjected to mock (NO siRNA/Control), negative control siRNA (NC siRNA/Control) and SRBI siRNA pretransfection (SRBI siRNA/Control), respectively (FIG. 7e). In contrast, whole-cell $Ca^{2+}$ currents in NC siRNA/apoCIII-treated cells were larger than those visualized in the afore-mentioned control cells (FIG. 7e). $Ca^2$ current density in SRBI siRNA/ApoCIII group (n=30) was significantly decreased in comparison with that in NC siRNA/apoCIII group (filled triangles, n=30) (FIG. 7f). The former is similar to, but the latter is significantly larger than that in NO siRNA/Control (n=30), NC siRNA/Control (n=29) or SRBI siRNA/Control (n=29) (FIG. 7f). The data verify that ApoCIII employs SRBI as an indispensable conveyor for signaling from this apoliprotein to β cell $Ca_V$ channels.

Discussion

The gross conductivity of $Ca_V$ channels depends on the density and activity of functional channels in the plasma membrane of the cell. Enhancement of whole-cell $Ca^{2+}$ currents by type 1 diabetic serum and its factor ApoCIII can result from enriched density and/or increased conductivity of functional $Ca_V$ channels in the β cell plasma membrane[4,5]. However, all studies[1,2,4,24] except one[4] have so far examined the effect of type 1 diabetic serum on $Ca_V$ channels only at the whole cell level. In the study by Juntti-Berggren et al, the increase in β cell $Ca_V$ channel activity by type 1 diabetic serum was characterized at both the single channel and the whole-cell level[4]. However, this work did not analyze whether type 1 diabetic serum could alter the density of functional $Ca_V$ channels in the β cell plasma membrane[4]. Although we have previously revealed that ApoCIII serves as a type 1 diabetic serum factor, hyperactivating β cell $Ca_V$ channels, only whole-cell patch-clamp analysis was performed[5]. Undoubtedly, detailed examination of biophysical properties of single $Ca_V$ channels in ApoCIII-treated cells should be implemented to mechanistically dissect hyperactivation of β cell $Ca_V$ channels by this apolipoprotein. Interestingly, cell-attached single channel recordings in the present work reveals that incubation with ApoCIII not only augments the activity of individual β cell $Ca_V1$ channels but also enriches the number of functional $Ca_V1$ channels in the recorded area of the β cell plasma membrane. The augmentation of single $Ca_V1$ channel activity is visualized as an increased open probability attributed to the prolonged mean open time and shortened mean closed time. Enrichment of number of functional $Ca_V1$ channels is verified by appearance of more levels of single $Ca_V1$ channel conductance.

The insulin-secreting RINm5F cell is equipped with $Ca_V1$, $Ca_V2$ and $Ca_V3$ channels[1,2]. We investigated if ApoCIII selectively hyperactivates $Ca_V1$ channels or indiscriminately impacts all these three types of $Ca_V$ channels in this insulin-secreting cell. It turned out that ApoCIII-induced hyperactivation of β cell $Ca_V$ channels could no longer take place following pharmacological ablation of $Ca_V1$ channels. This means that ApoCIII selectively hyperactivates $Ca_V1$ channels, which are the major $Ca_V$ channel type playing a predominant role over other types of $Ca_V$ channels in β cell physiology and pathophysiology. The selective hyperactivation of β cell $Ca_V1$ channels by ApoCIII accounts for the pathophysiological role of this apolipoprotein in $Ca^{2+}$-dependent β cell death[1,2,5].

A series of protein kinases, such as PKA and PKC, can effectively phosphorylate $Ca_V$ channels resulting in increases in the open channel density and activity due to phosphorylation-induced conformational changes in these channels[3,25,26]. Increases in the number and open probability of functional $Ca_V$ channels by ApoCIII might be mediated by protein kinases. ApoCIII has been demonstrated to activate PKC through β1 integrin in monocytic cells[16]. Furthermore, β1 integrin activation can also upregulate $Ca_V1$ channels in neurons, ventricular myocytes and vascular smooth muscle cells through stimulation of PKA, PKC and Src kinase[19-22]. All these components are present in β cells[2,27,30] and may suggest that ApoCIII employs the β1 integrin-PKA/PKC/Src kinase cascade to hyperactivate β cell $Ca_V$ channels. Indeed, the present work shows that complex inhibition of PKA, PKC and Src kinase effectively abrogates ApoCIII-induced hyperactivation of β cell $Ca_V$ channels and that coinhibition of PKA and Src kinase is enough for this effect. However, individual inhibition of PKA, PKC or Src kinase only produced, if anything, a marginal effect on ApoCIII-induced hyperactivation of β cell $Ca_V$ channels. Hence, we conclude that ApoCIII relies on parallel PKA and Src pathways to upregulate β cell $Ca_V$ channels.

Occurrence of ApoCIII-induced hyperactivation of β cell $Ca_V$ channels requires overnight incubation. Hence, the effect might be accounted for by an increase in $Ca_V$ channel expression. Therefore, we quantified immunoreactivities of $Ca_V1.2$ and $Ca_V1.3$ subunits in RINm5F cells following overnight incubation with ApoCIII. However, the incubation had no influence on β cell $Ca_V1$ channel expression. We therefore excluded the possibility that ApoCIII elevates β cell $Ca_V1$ channel expression.

The transmembrane receptor β1 integrin is noncovalently associated with other integrins to form a set of heterodimers. They recognize a large number of soluble and surface-bound proteins to mediate cell-cell, cell-extracellular matrix and cell-pathogen interactions[31]. β1 Integrin is situated downstream of ApoCIII and upstream of PKA/PKC/Src kinase in some cell types[16,19-22]. This made us investigate whether the ApoCIII-β1 integrin-PKA/PKC/Src kinase pathway operates in the β cell as the mechanism whereby this apolipoprotein hyperactivates $Ca_V1$ channels. Interestingly, knockdown of β1 integrin does not influence β cell $Ca_V$ channel activity in the absence of ApoCIII, but significantly abrogates ApoCIII-induced hyperactivation of β cell $Ca_V$ channels. The results clearly verify that β1 integrin plays a significant role in mediating the action of ApoCIII on β cell $Ca_V1$ channel activity.

Although β1 integrin can couple ApoCIII to the corresponding downstream effectors PKA, PKC and Src kinase, β1 integrin is unlikely to directly interact with this apolipoprotein[16,19-22]. Previous work shows that SRBI not only physically associates with ApoCIII but also interacts with β1 integrin[10,23]. This pinpoints the possibility that SRBI may serve as a molecular bridge between ApoCIII and β1 integrin with regard to β cell $Ca_V$ channel hyperactivation. Indeed, in the present study we could demonstrate that SRBI serves as a molecular bridge since SRBI gene silencing efficiently nullifies ApoCIII-induced hyperactivation of β cell $Ca_V$ channels. This generates a complete picture of the novel cascade of β cell $Ca_V$ channel hyperactivation, namely ApoCIII-SRBI-β1 integrin-PKA/Src.

ApoCIII-induced hyperactivation of β cell CaV1 channels observed in the present work occurred when cells were depolarized to more positive potentials than +10 mV. The effect of ApoCIII was detected by using the perforated whole-cell patch-clamp recording mode under experimental conditions where 10 mM Ca2+ was added in extracellular solution to obtain optimal Ca2+ currents. Such a high concentration of extracellular Ca2+ (10 mM) in comparison with physiological concentration of extracellular Ca2+ (2.5 mM) can significantly shift the I-V curve to more positive potentials. The perforated whole-cell patch-clamp recording mode has a similar effect. Hence, under in vivo conditions ApoCIII is likely to affect β cell CaV1 currents within the physiological membrane potential range.

In conclusion, our findings demonstrate that ApoCIII selectively hyperactivates β cell $Ca_V1$ channels through parallel PKA and Src kinase pathways in a SRBI/β1 integrin-dependent fashion. ApoCIII-induced hyperactivation of β cell $Ca_V1$ channels is characterized by the enriched density and increased activity of functional $Ca_V1$ channels in the β cell plasma membrane. Undoubtedly, this novel signal-transduction pathway has a potential to serve as an innovative drug discovery platform for the prevention of $Ca^{2+}$-dependent β cell death in association with diabetes.

Methods

Cell Culture and Treatments.

Islets of Langerhans were isolated from adult male and female mice and dispersed into single β cells. RINm5F cells at about 70% confluency were trypsinized. The resultant suspension of cells was seeded into Petri dishes or 12-well plates. The cells were cultivated in RPMI 1640 medium supplemented with 10% fetal bovine serum, 2 mM L-glutamine, and 100 U/100 µg/ml penicillin/streptomycin (Invitrogen, Carlsbad, Calif.) and maintained at 37° C. in a humidified 5% $CO_2$ incubator. They were grown overnight and then subjected to siRNA transfection. For patch-clamp analysis, cells underwent overnight treatment with ApoCIII, the PKA inhibitor H-89 (Calbiochem, La Jolla, Calif.), the PKC inhibitor calphostin C (Calbiochem), the Src kinase inhibitor PP2 (Calbiochem) and the $Ca_V1$ channel blocker nimodipine (Calbiochem) in RPMI medium at final concentrations of 20 µg/ml, 0.5 µM, 0.1 µM, 0.1 µM and 5 µM, respectively. ApoCIII was dissolved in 0.1% triflouroacetic acid (TFA) to make a stock solution of 1 mg/ml, whereas H-89, calphostin C, PP2 and nimodipine were dissolved in dimethyl sulfoxide (DMSO) to form stock solutions of 5 mM, 1 mM, 1 mM and 10 mM, respectively. 0.002% TFA and/or 0.03% DMSO were used as vehicle controls.

siRNA Design and Transfection.

Two pairs of 21-mer siRNA duplexes targeting the rat β1 integrin (β1 integrin siRNA #1, ID127971 and (31 integrin siRNA #2, ID127972) and SRBI (ID128929) were designed and chemically synthesized by Applied Biosystems/Ambion (Austin, Tex.). Their sequences were subjected to BLAST search to ensure their specificity. Silencer® Select Negative Control siRNA (4390843), not targeting any gene product, and Silencer® Select GAPDH Positive Control siRNA (4390849), efficiently silencing GAPDH in human, mouse, and rat cells, were purchased from Applied Biosystems/Ambion (Austin, Tex.). RINm5F cells were reversely transfected with Lipofectamine™ RNAiMAX. Briefly, negative control siRNA, β1 integrin siRNA #1, β1 integrin siRNA #2 or SRBI siRNA was mixed with Lipofectamine™ RNAiMAX followed by 20-min incubation at room temperature. Subsequently, cells were added to the siRNA/Lipofectamine™ RNAiMAX mixtures followed by gentle agitation and kept at 37° C. in a humidified 5% $CO_2$ incubator. After 72 h, the transfected cells were grown to about 70% confluency and subjected to immunoblot assay or different treatments.

Semiquantitative RT-TCR.

Total RNA was isolated from RINm5F cells using the RNeasy Micro Kit as recommended by the manufacturer (Qiagen, Valencia, Calif.). RT-PCR primer pairs were synthesized by Sigma-Aldrich (St. Louis, Mo.). The SRBI primer pair consisted of the forward primer 5'-CAAGAAGC-CAAGCTGTAGGG-3' (SEQ ID NO: 11) and the reverse primer 5'-CCCAACAGGCTCTACTCAGC-3' (SEQ ID NO: 12). The GAPDH primer pair comprised the forward primer 5'-TAGACAAGATGGTGAAGG-3' (SEQ ID NO: 13) and the reverse primer 5'-TCCTTGGAGGCCATGTAG-3'(SEQ ID NO: 14). 500 ng of total RNA was reverse transcribed with SuperScript® II Reverse Transcriptase (Invitrogen) and Oligo(dT)12-18 Primer (Invitrogen). Polymerase chain reaction was carried out using the Platinum® Taq DNA Polymerase (Invitrogen). It underwent 90 seconds at 94° C. for completely denaturing templates and activating the Taq DNA Polymerase, followed by 29 cycles of denaturing at 94° C. for 30 seconds, annealing at 55° C. for 30 seconds and extension at 72° C. for 30 seconds, and ending with a final extension at 72° C. for 5 min. The amplified PCR products were detected by agarose gel electrophoresis and ethidium bromide staining.

SDS-PAGE and Immunoblot Analysis.

RINm5F cells following different treatments were lysed in a lysis buffer (pH 7.5) consisting of 50 mM HEPES, 150 mM NaCl, 1 mM EGTA, 1 mM EDTA, 10% glycerol, 1% triton X-100, 1 mM PMSF and a protease inhibitor cocktail (Roche Diagnostics, Mannheim, Germany). The lysate was centrifuged at 800×g for 10 min at 4° C. to remove cell debris and nuclei. The protein concentration of the resulting samples was determined with Bio-Rad protein assay reagent (Bio-Rad, Hercules, Calif.). The samples were denatured by heating at 96° C. for 3 min in SDS sample buffer and then underwent sodium dodecyl sulfate-polyacrylamide gel electrophoresis (SDS-PAGE) and immunoblot analysis. Briefly, 50, 90 or 180 μg proteins were separated in discontinuous gels consisting of a 4% acrylamide stacking gel (pH 6.8) and an 8% acrylamide separating gel (pH 8.8). The separated proteins were then electroblotted to hydrophobic polyvinylidene difluoride membrane (Hybond-P; GE Healthcare, Uppsala, Sweden). The blots were blocked by incubation for 1 h with 5% non-fat milk powder in a washing buffer, containing 50 mM tris(hydroxymethyl)aminomethane, 150 mM NaCl and 0.05% Tween 20 (pH 7.5). They were then incubated overnight at 4° C. with affinity-purified rabbit polyclonal antibodies to β1 integrin (1:500; Millipore, Billerica, Mass.), SRBI (1:2500; Novus, Cambridge, UK), $Ca_V1.2$ (1:200) and $Ca_V1.3$ (1:200), respectively, and for 1 h at room temperature with mouse monoclonal antibody to glyceraldehyde-3-phosphate dehydrogenase (GAPDH, 1:4000; Applied Biosystems/Ambion, Austin, Tex.), respectively. After rinsing with the washing buffer, the blots were incubated with the secondary antibodies (either horseradish peroxidase-conjugated goat anti-rabbit IgG or horseradish peroxidase-conjugated goat anti-mouse IgG; 1:50,000; Bio-Rad, Hercules, Calif.) at room temperature for 45 min. The immunoreactive bands were visualized with the ECL plus Western blotting detection system (GE Healthcare, Uppsala, Sweden).

Electrophysiology.

Mouse islet cells and RINm5F cells following different treatments were subjected to single channel and whole-cell patch-clamp measurements. Cell-attached and perforated whole-cell patch-clamp configurations were employed. Electrodes were made from borosilicate glass capillaries, fire-polished and coated with Sylgard close to their tips. Some of them were filled with a solution containing (in mM) 110 $BaCl_2$, 10 TEA-Cl, and 5 HEPES (pH 7.4 with $Ba(OH)_2$) for single channel measurements. Others were filled with a solution composed of (in mM) 76 $Cs_2SO_4$, 1 $MgCl_2$, 10 KCl, 10 NaCl, and 5 HEPES (pH 7.35 with CsOH), as well as amphotericin B (0.24 mg/ml) for whole-cell current recordings. Electrode resistance ranged between 4 and 6 MΩ when they were filled with electrode solutions and immersed in bath solutions. The electrode offset potential was corrected in bath solutions prior to gigaseal formation. Single-channel recordings were performed with cells bathed in a depolarizing external recording solution, containing (in mM) 125 KCl, 30 KOH, 10 EGTA, 2 $CaCl_2$, 1 $MgCl_2$, and 5 HEPES-KOH (pH 7.15). This solution was used to bring the intracellular potential to 0 mV. For perforated whole-cell current measurements, the cells were bathed in a solution containing (in mM) 138 NaCl, 5.6 KCl, 1.2 $MgCl_2$, 10 $CaCl_2$, 5 HEPES (pH 7.4). Single channel and whole-cell currents were recorded with an Axopatch 200B amplifier (Molecular Devices, Foster City, Calif.) and an EPC-9 patch clamp amplifier (HEKA Elektronik, Lambrecht/Pfalz, Germany), respectively, at room temperature (about 22° C.). Acquisition and analysis of single channel and whole-cell current data were done using the software program pCLAMP 10 (Axon Instruments) and the software program PatchMaster/FitMaster (HEKA), respectively. The amplitude of whole-cell currents was normalized by the cell capacitance.

Statistical Analysis.

All data are presented as mean±SEM. Statistical significance was determined by one-way ANOVA, followed by least significant difference (LSD) test. When two groups were compared, unpaired Student's t test or Mann-Whitney U test was employed. The significance level was set to 0.05 or 0.01.

REFERENCES

1. Yang, S. N. & Berggren, P. O. β-Cell $Ca_V$ channel regulation in physiology and pathophysiology. *Am. J. Physiol.* 288, E16-E28 (2005).
2. Yang, S. N. & Berggren, P. O. The role of voltage-gated calcium channels in pancreatic β-cell physiology and pathophysiology. *Endocr. Rev.* 27, 621-676 (2006).
3. Catterall, W. A. Structure and regulation of voltage-gated $Ca^{2+}$ channels. *Annu. Rev. Cell Dev. Biol.* 16, 521-555 (2000).
4. Juntti-Berggren, L. et al. Increased activity of L-type $Ca^{2+}$ channels exposed to serum from patients with type I diabetes. *Science* 261, 86-90 (1993).
5. Juntti-Berggren, L. et al. Apolipoprotein CIII promotes $Ca^{2+}$-dependent β cell death in type 1 diabetes. *Proc. Natl. Acad. Sci. USA* 101, 10090-10094 (2004).

6. Sol, E. M., Sundsten, T. & Bergsten, P. Role of MAPK in apolipoprotein CIII-induced apoptosis in INS-1E cells. *Lipids Health Dis.* 8, 3 (2009).
7. Holmberg, R. et al. Lowering apolipoprotein CIII delays onset of type 1 diabetes. *Proc. Natl. Acad. Sci. USA* 108, 10685-10689 (2011).
8. Gangabadage, C. S. et al. Structure and dynamics of human apolipoprotein CIII. *J. Biol. Chem.* 283, 17416-17427 (2008).
9. Jong, M. C., Hofker, M. H. & Havekes, L. M. Role of ApoCs in lipoprotein metabolism: functional differences between ApoC1, ApoC2, and ApoC3. *Arterioscler. Thromb. Vasc. Biol.* 19, 472-484 (1999).
10. Xu, S. et al. Apolipoproteins of HDL can directly mediate binding to the scavenger receptor SR-BI, an HDL receptor that mediates selective lipid uptake. *J. Lipid Res.* 38, 1289-1298 (1997).
11. Clayey, V., Lestavel-Delattre, S., Copin, C., Bard, J. M. & Fruchart, J. C. Modulation of lipoprotein B binding to the LDL receptor by exogenous lipids and apolipoproteins CI, CII, CIII, and E. *Arterioscler. Thromb. Vasc. Biol.* 15, 963-971 (1995).
12. Huard, K. et al. Apolipoproteins C-II and C-III inhibit selective uptake of low- and high-density lipoprotein cholesteryl esters in HepG2 cells. *Int. J. Biochem. Cell Biol.* 37, 1308-1318 (2005).
13. Chan, D. C., Watts, G. F., Redgrave, T. G., Mori, T. A. & Barrett, P. H. Apolipoprotein B-100 kinetics in visceral obesity: associations with plasma apolipoprotein C-III concentration. *Metabolism* 51, 1041-1046 (2002).
14. Sundsten, T., Ostenson, C. G. & Bergsten, P. Serum protein patterns in newly diagnosed type 2 diabetes mellitus—influence of diabetic environment and family history of diabetes. *Diabetes Metab. Res. Rev.* 24, 148-154 (2008).
15. Atzmon, G. et al. Lipoprotein genotype and conserved pathway for exceptional longevity in humans. *PLoS Biol.* 4, e113 (2006).
16. Kawakami, A. et al. Apolipoprotein CIII in apolipoprotein B lipoproteins enhances the adhesion of human monocytic cells to endothelial cells. *Circulation* 113, 691-700 (2006).
17. Fang, D. Z. & Liu, B. W. Apolipoprotein C-III can specifically bind to hepatic plasma membranes. *Mol. Cell. Biochem.* 207, 57-64 (2000).
18. Kawakami, A. et al. Apolipoprotein CIII-induced THP-1 cell adhesion to endothelial cells involves *pertussis* toxin-sensitive G protein- and protein kinase Cα-mediated nuclear factor-κB activation. *Arterioscler. Thromb. Vasc. Biol.* 27, 219-225 (2007).
19. Rueckschloss, U. & Isenberg, G. Contraction augments L-type $Ca^{2+}$ currents in adherent guinea-pig cardiomyocytes. *J. Physiol.* 560, 403-411 (2004).
20. Waitkus-Edwards, K. R. et al. $\alpha_4\beta_1$ Integrin activation of L-type calcium channels in vascular smooth muscle causes arteriole vasoconstriction. *Circ. Res.* 90, 473-480 (2002).
21. Wu, X., Davis, G. E., Meininger, G. A., Wilson, E. & Davis, M. J. Regulation of the L-type calcium channel by $\alpha_5\beta_1$ integrin requires signaling between focal adhesion proteins. *J. Biol. Chem.* 276, 30285-30292 (2001).
22. Gui, P. et al. Integrin receptor activation triggers converging regulation of Cav1.2 calcium channels by c-Src and protein kinase A pathways. *J. Biol. Chem.* 281, 14015-14025 (2006).
23. Bamberger, M. E., Harris, M. E., McDonald, D. R., Husemann, J. & Landreth, G. E. A cell surface receptor complex for fibrillar beta-amyloid mediates microglial activation. *J. Neurosci.* 23, 2665-2674 (2003).
24. Ristic, H., Srinivasan, S., Hall, K. E., Sima, A. A. & Wiley, J. W. Serum from diabetic BB/W rats enhances calcium currents in primary sensory neurons. *J. Neurophysiol.* 80, 1236-1244 (1998).
25. Kavalali, E. T., Hwang, K. S. & Plummer, M. R. cAMP-dependent enhancement of dihydropyridine-sensitive calcium channel availability in hippocampal neurons. *J. Neurosci.* 17, 5334-5348 (1997).
26. Yang, J. & Tsien, R. W. Enhancement of N- and L-type calcium channel currents by protein kinase C in frog sympathetic neurons. *Neuron* 10, 127-136 (1993).
27. Mukai, E. et al. Exendin-4 suppresses Src activation and reactive oxygen species production in diabetic Goto-Kakizaki rat islets in an Epac-dependent manner. *Diabetes* 60, 218-226 (2011).
28. Kantengwa, S. et al. Identification and characterization of a3β1 integrin on primary and transformed rat islet cells. *Exp. Cell Res.* 237, 394-402 (1997).
29. Bosco, D., Meda, P., Halban, P. A. & Rouiller, D. G. Importance of cell-matrix interactions in rat islet β-cell secretion in vitro: role of a6β1 integrin. *Diabetes* 49, 233-243 (2000).
30. Nikolova, G. et al. The vascular basement membrane: a niche for insulin gene expression and β cell proliferation. *Dev. Cell* 10, 397-405 (2006).
31. Luo, B. H., Carman, C. V. & Springer, T. A. Structural basis of integrin regulation and signaling. *Annu. Rev. Immunol.* 25, 619-647 (2007).

We claim:

1. A method for identifying candidate compounds for limiting development of and/or treating diabetes, comprising
    a) contacting a first population of insulin secreting cells with an amount of ApoCIII effective to increase density and/or conductivity of $Ca_v1$ channels, in the presence of one or more test compounds; and
    b) identifying those positive test compounds that inhibit the ApoCIII-induced increase in density and/or conductivity of $Ca_v1$ channels and that inhibit SRBI expression or activity in the first population of insulin secreting cells compared to control, wherein the control comprises contacting a second population of insulin secreting cells with an amount of ApoCIII effective to increase density and/or conductivity of $Ca_v1$ channels, in the absence of test compounds;
        wherein the positive test compounds are candidate compounds for limiting development of and/or treating diabetes.

2. The method of claim 1 wherein the insulin-secreting cells are pancreatic β cells.

3. The method of claim 2, wherein the method comprises contacting the cells with ApoCIII for at least 6 hours.

4. The method of claim 2, wherein the candidate compounds are candidate compounds for limiting development of and/or treating type 1 diabetes.

5. The method of claim 2, wherein the candidate compounds are candidate compounds for limiting development of and/or treating type 2 diabetes.

6. The method of claim 1, wherein the method comprises contacting the cells with ApoCIII for at least 6 hours.

7. The method of claim 6, wherein the candidate compounds are candidate compounds for limiting development of and/or treating type 1 diabetes.

8. The method of claim 6, wherein the candidate compounds are candidate compounds for limiting development of and/or treating type 2 diabetes.

9. The method of claim 1, wherein the candidate compounds are candidate compounds for limiting development of and/or treating type 1 diabetes.

10. The method of claim 1, wherein the candidate compounds are candidate compounds for limiting development of and/or treating type 2 diabetes.

* * * * *

SEQUENCE LISTING

```
<160> NUMBER OF SEQ ID NOS: 14

<210> SEQ ID NO 1
<211> LENGTH: 487
<212> TYPE: DNA
<213> ORGANISM: Homo sapiens
<220> FEATURE:
<221> NAME/KEY: CDS
<222> LOCATION: (1)..(300)

<400> SEQUENCE: 1 atg cag ccc cgg gta ctc ctt gtt gtt gcc ctc ctg gcg ctc ctg gcc      48
Met Gln Pro Arg Val Leu Leu Val Val Ala Leu Leu Ala Leu Leu Ala
1               5                   10                  15 tct gcc cga gct tca gag gcc gag gat gcc tcc ctt ctc agc ttc atg      96
```

```
                 Ser Ala Arg Ala Ser Glu Ala Glu Asp Ala Ser Leu Leu Ser Phe Met
                                  20                  25                  30 cag ggt tac atg aag cac gcc acc aag acc gcc aag gat gca ctg agc          144
Gln Gly Tyr Met Lys His Ala Thr Lys Thr Ala Lys Asp Ala Leu Ser
                 35                  40                  45 agc gtg cag gag tcc cag gtg gcc cag cag gcc agg ggc tgg gtg acc          192
Ser Val Gln Glu Ser Gln Val Ala Gln Gln Ala Arg Gly Trp Val Thr
     50                  55                  60 gat ggc ttc agt tcc ctg aaa gac tac tgg agc acc gtt aag gac aag          240
Asp Gly Phe Ser Ser Leu Lys Asp Tyr Trp Ser Thr Val Lys Asp Lys
 65                  70                  75                  80 ttc tct gag ttc tgg gat ttg gac cct gag gtc aga cca act tca gcc          288
Phe Ser Glu Phe Trp Asp Leu Asp Pro Glu Val Arg Pro Thr Ser Ala
                     85                  90                  95 gtg gct gcc tga gacctcaata ccccaagtcc acctgcctat ccatcctgcc              340
Val Ala Ala agctccttgg gtcctgcaat ctccagggct gcccctgtag gttgcttaaa agggacagta        400
ttctcagtgc tctcctaccc cacctcatgc ctggcccccc tccaggcatg ctggcctccc        460
aataaagctg acaagaagc tgctatg                                             487

<210> SEQ ID NO 2
<211> LENGTH: 99
<212> TYPE: PRT
<213> ORGANISM: Homo sapiens

<400> SEQUENCE: 2

Met Gln Pro Arg Val Leu Leu Val Val Ala Leu Leu Ala Leu Leu Ala
 1               5                  10                  15

Ser Ala Arg Ala Ser Glu Ala Glu Asp Ala Ser Leu Leu Ser Phe Met
                 20                  25                  30

Gln Gly Tyr Met Lys His Ala Thr Lys Thr Ala Lys Asp Ala Leu Ser
                 35                  40                  45

Ser Val Gln Glu Ser Gln Val Ala Gln Gln Ala Arg Gly Trp Val Thr
     50                  55                  60

Asp Gly Phe Ser Ser Leu Lys Asp Tyr Trp Ser Thr Val Lys Asp Lys
 65                  70                  75                  80

Phe Ser Glu Phe Trp Asp Leu Asp Pro Glu Val Arg Pro Thr Ser Ala
                     85                  90                  95

Val Ala Ala

<210> SEQ ID NO 3
<211> LENGTH: 2509
<212> TYPE: DNA
<213> ORGANISM: Rattus norvegicus

<400> SEQUENCE: 3
taaagagacg gatgacctac agccccaggc ccacccattc aacaggccta gctcattccc         60
aagcccagac atcaaggcat gggacaccca cgcatggcag cttcgtgtcc agctttatta       120
gggacagcat gtttaggtga ggtctgggga gggataaagg catgagaata ctttccccc        180 ttagagcaac cttcggaggc agcaggatag atgccagac acatctggaa catggaggtc        240
tcacggctca agagttggtg ttgttagttg gtcctcaggg ccagactccc agaggccagt       300
gaacttatca gtgaacttgc tccagtagcc tttcagggat ttgaagcgat tgtccatcca       360 gccccttgggg gttaaaacag taataggtgt gtgtgtgtgt gtgtgtgtgt gtgtgtgtgt       420
gtgtgtgtgt gtgtgtgtgt gaaaagatct cctgtgggca gctagaccca ggggtgcacc       480
```

```
taggcctcca ctggctccct aagccaccag caccacctta cctagcacca ccctcagaat    540
cacctgcagc taccactcaa ggtggaggag atggtaaagg ctaagaaaac ccaccttcat    600
cagagcccca ttacctcccg tccaatctct cttcaggcct gaggcaccaa ccactgggga    660
ggtggatact aaggtcagct tgcctttgta gtccatagaa acagtgtcct tgaggtgtcc    720
catccctggc tctaagtgga tggatcaagg gaggggtgaa ctttctgttt ggaaacatta    780
ccagagggct tctaagctct gtgatctagg ccaggttatc taactctttc ccagctgcgg    840
aggtagatag tacctctcca caacctgttc tgggcacaga gactgtcaac atcttttgct    900
acataggcaa tgatcaaatg tcacgtaaac gattggcagg gtaatgtttc atcacgggca    960
agatgcctca cttaggttga gcccagggat ggaaacaggg cagaaccccc aacccgtaat   1020
gctcaacctt ccaacttccc tgtaatcaga gcaggaaggc ctcccagagc cacccctaga   1080
ccctgtgctc aaagaagaaa acctgcaggg aggctgaacg ctcctcaggc tgctctgagg   1140
agaagcagag gagatagaag aagtctgctt gcactgcctg tcatcttagt cacagtcccc   1200
agcaaaggcc ccgtgagaga ctggatgctc agacgggccc aagaccctgg taaacttggt   1260
gggccacagt ctccgtgtcc agggcctcag caccagggca ggaggggcga ggaccaggaa   1320
aggaggtccg tgtgcatacc tggccaccac agctatatca gactcctgca tgctgcttag   1380
tgcatcctgg accgtcttgg aggcttgttc catgtagccc tgcatagagc ccagcagcaa   1440
ggatccctct ccctcatcag ctcctgcaag agagcagagt tgagccaggc cagccctcag   1500
ctcttgccca gccatcgctt ttcagggtag ggtccccaga ccagctcccg cagaaatccc   1560
agccccactt ccaccagctt acgggcagag gccaggagag ccacgagggc cacgatgagg   1620
agcattcggg gctgcatggc acctgtgcac ctgcgggaga ccatcttgtg agagggtatt   1680
gtggatctcc acatctaagc ccttccctgg agaacaccac ggcccctctg tcatgaatcc   1740
ccaagccttt ctcctactga tatcagctct cggagagaga actaagaaga cccagaccca   1800
ccccaagggg ctggaaggtg gaatgtggga atcctctgca aagcagaaca tctacccagc   1860
ctctgcccca atatatggag aaacaacagg tttcttttc tctctaggct tcaggctttt   1920
cagtctgggg taggcacgga tatcaaaggc ttctaatagc tcagagcaag acgaacaagg   1980
ggcagcatga cccagttccc aatcagctct gccactaccc agtgcaaggc ttttttgccc   2040
agtggcctcc ctttcctcag cttctagcct cccccaccca ccaggatacc caagggctgg   2100
aggccgtgaa ttccaagcat tctgtaggct agctggctga gtggccagag cgtcttctct   2160
ctgtctcctc cctcccttcc tctcctcccc agggcattca cctggagtag ctagctgctt   2220
ctagggataa aactgggcag gcaagccggg acgctctgat ctgttttata ttggctccag   2280
gatgggacag cgggcacaga aggcccagtg agctggtcaa aggtcacctg ctgaacagtc   2340
cagaccagag cccgaggcag ggaggccatg cagccagctg ccagaggagt tgagaaatcc   2400
ctcagagatt gccacaccg ttcacttcca cctccgcagc caagagatca gctactgacc   2460
tgcctcgatg agactggtga gacaggaaaa gactcagggg acaagcctt                2509
```

<210> SEQ ID NO 4
<211> LENGTH: 101
<212> TYPE: PRT
<213> ORGANISM: Rattus norvegicus

<400> SEQUENCE: 4

```
Met Gln Pro Arg Met Leu Leu Ile Val Ala Leu Val Ala Leu Leu Ala
1               5                   10                  15
```

-continued

```
Ser Ala Arg Ala Asp Glu Gly Glu Gly Ser Leu Leu Gly Ser Met
         20                  25                  30

Gln Gly Tyr Met Glu Gln Ala Ser Lys Thr Val Gln Asp Ala Leu Ser
             35                  40                  45

Ser Met Gln Glu Ser Asp Ile Ala Val Val Ala Ser Arg Gly Trp Met
 50                  55                  60

Asp Asn Arg Phe Lys Ser Leu Lys Gly Tyr Trp Ser Lys Phe Thr Asp
 65                  70                  75                  80

Lys Phe Thr Gly Leu Trp Glu Ser Gly Pro Glu Asp Gln Leu Thr Thr
                 85                  90                  95

Pro Thr Leu Glu Pro
            100
```

<210> SEQ ID NO 5
<211> LENGTH: 3262
<212> TYPE: DNA
<213> ORGANISM: Macaca fascicularis
<220> FEATURE:
<221> NAME/KEY: CDS
<222> LOCATION: (858)..(912)
<220> FEATURE:
<221> NAME/KEY: CDS
<222> LOCATION: (1048)..(1171)
<220> FEATURE:
<221> NAME/KEY: CDS
<222> LOCATION: (2871)..(2988)

<400> SEQUENCE: 5

```
ctgcagggct ggcgggacag cagcatggac acagtctcct ggggatttcc caactctccc      60
gccagcttgc tgcctctggc cgccctgcct caggccctgg tctctgatca gcaggtgacc     120
tttgcccagt gccctgggtc ctcagtgcct gctgccctgg agacaatata aacaggctc      180 agaaccctcc tgcctgcctg ctctgttcat ccctagaggc agctgctcca ggtaatgccc     240
tctggggagg ggaaagagga ggggaggagg atgaagagga gcaagaggag ctccctgccc     300
agcccagcca gcaagcctgg agaaacactt gctagagcta aggaagcctc ggagctggac     360
gggtgccccc aaccctcat cataacctga agaaaatgga ggcccgggag gggtgtcact      420
tgcccaaagc tacacagggg gtggggctgg aaatggttcc aagtgcaggc ttccccgtca     480
ttctgcaggc ttagggctgg aggaagcctt agacagccca gtcctaccca gacagggaaa     540
ctgaggcctg gagagggcca gaaagcccca aagtcacaca gcatgttggc tgcactggac     600
agagaccagt ccagaccgca ggtgccttga tgtccagtct ggtgggtttt ctgctccatc     660
ccacctacct cccttttgggc ccctcactag tccccttctg agagcccgta ttagcaggaa    720 gcaggccccct actccctctg gcagaccgag ctcaggtccc accttagggg ccatgccacc    780
tgtccaggga ggggtccaga ggcatggggg cctgggtgc ccctcacagg acaattcctt      840
gcaggaacag aggcgcc atg cag ccc cgg gta ctc ctt gtt gct gcc ctg        890
                    Met Gln Pro Arg Val Leu Leu Val Ala Ala Leu
                     1               5                  10 ctg tca ctc ctg gcc tct gcc a gtaagcactt ggtgggactg gctgggggc          942
Leu Ser Leu Leu Ala Ser Ala
             15 aggatggagg tggcttgggg atcccagtcc taatgggtgg tcaagcagga gctcagggct     1002 cgcctagagg ccgatccacc actctcagcc ctgctctttc ctcag ga  gct tca gag     1058
                                                    Arg Ala Ser Glu
                                                             20 gcc gag gac acc tcc ctt ctt ggc ttc atg cag ggc tac atg cag cat       1106
```

```
Ala Glu Asp Thr Ser Leu Leu Gly Phe Met Gln Gly Tyr Met Gln His
         25                  30                  35 gcc acc aag acc gcc aag gat gca ctg acc agc gtc cag gag tcc cag    1154
Ala Thr Lys Thr Ala Lys Asp Ala Leu Thr Ser Val Gln Glu Ser Gln
         40                  45                  50 gtg gcc cag cag gcc ag gtacaccgc tggcctccct ccccatccct             1201
Val Ala Gln Gln Ala Arg
 55              60 catgccagct ccctccattc cacccgccc tgcctggtg agatcccagc aatggaatgg    1261
aggtgccagc ctcccctggt cctgtgcctc tttggcctcc tctttcctca cagggccttg  1321
gtcaggctgc tgtgggagag acgacagagt tgagactgcg ttcccccggg tccctccctt  1381
tctcccagag cagttctagg gtgggccatt ttagccctca tttccatttt cctttccttt  1441
tctttctttt tcttttcttt tttttctttt ctttcttttt tttttttgag atggagtctc  1501
cctctgtcac ccaggctaga gtgcagtggt gcgatctcag cggatctcgg ctcactgcaa  1561
cctctgcctc ccaggttcac ccattctcc tgcctcagcc tcccaagtag ctgggattac   1621
aggcgtgcca ccacatccag ctacttttg tatttttctc agagacgggg tttccccatg   1681
ttggacaggc tggtcttgaa ctcctgacct caggtgatct gcctacctcg gcctcccaaa  1741
ttgctgggat tacaggcatg agccactgcg cctgacccca ttttccttt ctgaaggtct   1801 ggctagagca gaggtcctca accttttgg caccagggac cagttttgtg gtagacagtt   1861
tttccatggg tcagcgggga tggcttgggg atgaaactgc tccacctcag atcaccaggc  1921
attggattct cctaagaagc cctccacccc gaccctggc atgcgcagtt cacaacaggt    1981
ttcacactcc tgtgagaatc taatgccgcc taacctgaca gaaggcgggg cttgggcggt  2041
attcctctgt cacccatcac tcactttgtg ctgtgcagcc tggctcctaa ctggccatgg  2101
accagtaccc atctgtgact gggggctgg ggaccctgg gctaggggtt tgccttggga    2161
ggccccacct ggcccaattc tagcctgggt atgagagtgc ttctgctttg ttccaagacc  2221
tggggccagg gtgagtagaa gtgtgtcctt cctctcccat cctgcccctg cccatcggtc  2281
ctctcctctc cctactccct tccccacctc accctgactg gcattggctg gcatagcaga  2341
ggttgtttat aagcattctt aatcctcaga accggctttg gggtaggtgt tattttccca  2401
ctttgcagat gagaaaattg aggctcagag cgattaggtg acctgcccca gatcacacaa  2461
ctaatcaatc ctccaatgac tttccaaatg agaggtcgcc tccctctgtc ctaccctgct  2521
cggaaccacc aggatataca actccagggg atactgtctg cacagaaaac aatgacagcc  2581
ttgacctttc acatctcccc accctgtcac tctgtgcctc aagcccaggg gcaaaaacat  2641
ctgaggtcac ctggagacgg cagggttcga cttgtgctgg ggttcctgta agggcatctc  2701
ttctcccagg gtgcagctg tgggcagtcc tgcctgaggt ctcagggctg ttgtccagtg   2761
aagttgagag ggtggcaggg agagccagtg gggacatggg tgtgggtccc atagttgcct  2821
ccaaaggagt tctcatgccc tgctctgttg cttcccctta ctgatttag a ggc tgg    2877
                                                          Gly Trp gtg acc gat ggc ttc agt tcc ctg aaa gac tac tgg agc acc gtt aag   2925
Val Thr Asp Gly Phe Ser Ser Leu Lys Asp Tyr Trp Ser Thr Val Lys
         65                  70                  75 gac aag tta tct ggg ttc tgg gat ttg aac cct gag gcc aaa ccc act   2973
Asp Lys Leu Ser Gly Phe Trp Asp Leu Asn Pro Glu Ala Lys Pro Thr
         80                  85                  90 ctg gct gag gct gcc tgagacctca atccccaag tccacctgcc tgtccatcct    3028
Leu Ala Glu Ala Ala
 95
```

```
gccagctcct tgggtcctgc agcctccagg gctgcccctg taggttgctt aaaagggaca      3088
gtattctcag tgccctccta ccgcacctca tgcctggccc cctccaggc agggtgtcct       3148 cccaataaag ctggacaaga agctgctatg agtgggccgt cacaagtgtg ccatctgtgt      3208
ctgggtatgg gaaagggtcc gaggctgttc tgtgggtagg cactggacga ctgc            3262
```

```
<210> SEQ ID NO 6
<211> LENGTH: 99
<212> TYPE: PRT
<213> ORGANISM: Macaca fascicularis

<400> SEQUENCE: 6
```

```
Met Gln Pro Arg Val Leu Leu Val Ala Ala Leu Leu Ser Leu Leu Ala
1               5                   10                  15

Ser Ala Arg Ala Ser Glu Ala Glu Asp Thr Ser Leu Leu Gly Phe Met
            20                  25                  30

Gln Gly Tyr Met Gln His Ala Thr Lys Thr Ala Lys Asp Ala Leu Thr
        35                  40                  45

Ser Val Gln Glu Ser Gln Val Ala Gln Gln Ala Arg Gly Trp Val Thr
    50                  55                  60

Asp Gly Phe Ser Ser Leu Lys Asp Tyr Trp Ser Thr Val Lys Asp Lys
65                  70                  75                  80

Leu Ser Gly Phe Trp Asp Leu Asn Pro Glu Ala Lys Pro Thr Leu Ala
                85                  90                  95

Glu Ala Ala
```

```
<210> SEQ ID NO 7
<211> LENGTH: 2411
<212> TYPE: DNA
<213> ORGANISM: Mus musculus
<220> FEATURE:
<221> NAME/KEY: CDS
<222> LOCATION: (54)..(350)

<400> SEQUENCE: 7
```

```
gctacatcag gggctgtgca gcgtcgccca tactccgagc aaagaactgt ggc cag         56
                                                        Gly Gln
                                                            1 agg cag tcg agg tta gtg agg act gcg agg cag aca ctt tgc tgt gtt       104
Arg Gln Ser Arg Leu Val Arg Thr Ala Arg Gln Thr Leu Cys Cys Val
        5                   10                  15 caa atc caa gtc aag ggt aca aaa atg cag agc aat aaa gcc ttt aac       152
Gln Ile Gln Val Lys Gly Thr Lys Met Gln Ser Asn Lys Ala Phe Asn
            20                  25                  30 ttg gag aag cag aat cat act cca agg aag cat cat cag cat cac cac       200
Leu Glu Lys Gln Asn His Thr Pro Arg Lys His His Gln His His His
        35                  40                  45 cag cag cac cat cag cag caa cag cag cag cag cag caa cag cca ccc       248
Gln Gln His His Gln Gln Gln Gln Gln Gln Gln Gln Gln Pro Pro
50                  55                  60                  65 cca cca ata cct gca aat ggc cag cag gcc agc agc cag aat gaa ggc       296
Pro Pro Ile Pro Ala Asn Gly Gln Gln Ala Ser Ser Gln Asn Glu Gly
                70                  75                  80 ttg act att gac ctg aag aat ttt agg aaa cca gga gag aag acc ttt       344
Leu Thr Ile Asp Leu Lys Asn Phe Arg Lys Pro Gly Glu Lys Thr Phe
            85                  90                  95 aca cag cgtagccgtc tctttgtggg caatcttccc cctgatatca ctgaggagga        400
Thr Gln
```

| | |
|---|---|
| aatgaggaaa ctatttgaga aatatggaaa agcaggcgaa gttttcattc ataaggataa | 460 |
| aggctttggc tttattcgct tggaaacacg aaccctagcg gaaattgtca agtggagct | 520 |
| ggacaacatg cccctccgtg ggaagcagct gcgagtgcgc ttcgcctgtc acagtgcatc | 580 |
| ccttacagtc cgcaaccttc ctcagtacgt gtcgaacgaa ctgctggaag aagcctttc | 640 |
| tgtgttcggc caggtggaga gggctgtagt cattgtggat gaccgaggaa ggccctcagg | 700 |
| gaaaggcatt gttgagttct cagggaagcc agctgctcgg aaagctctgg acagatgcag | 760 |
| tgaaggctcc ttcttgctga ctacatttcc ttggcctgtg actgtggagc ctatggacca | 820 |
| gttagatgat gaagagggac ttccagaaaa actggttata aaaaaccagc aattccacaa | 880 |
| ggagagagaa cagccaccca gatttgcaca acctggctcc tttgagtatg agtatgccat | 940 |
| gcgctggaag gcactcattg agatggaaa gcaacagcag gatcaagtgg atcggaacat | 1000 |
| caaggaggct cgtgagaagc tggagatgga gatggaggct gcacgtcatg agcaccaggt | 1060 |
| tatgctaatg aggcaggatt tgatgagacg tcaagaagag cttcggagaa tggaggagct | 1120 |
| gcataaccaa gaggttcaga agcgaaagca gttagaactc aggcaggaag aggaacgcag | 1180 |
| gcgccgtgag gaagagatgc ggcgacaaca agaggaaatg atgcgccgac agcaggaagg | 1240 |
| attcaaggga accttccctg atgcgagaga acaagagata cggatgggcc aaatggctat | 1300 |
| gggaggtgct atgggcataa acaatagagg cgcgatgccc cctgctcctg tgccacctgg | 1360 |
| tactccagct cctccaggac ctgccactat gatgccagat ggaacccttg gattgacccc | 1420 |
| accaacaact gaacgttttg gccaagctgc aacaatggaa ggaattggag caattggtgg | 1480 |
| aactcctcct gcattcaacc gtccagctcc gggagctgaa tttgctccaa ataaacgccg | 1540 |
| ccgatattag ataaagttgc attgtctagt ttcctgcagc ccttaaaaga agggccctt | 1600 |
| ttggactagc cagaattcta ccctggaaaa gtgttagggg ttcttcccaa tagataggcc | 1660 |
| ttccctgctt gtactactct agggatcatg cttgaagtca gagggcaga gaaggggtgg | 1720 |
| tattcaacaa gtcaaagtct gtggtatatt gctttatcaa gactgtctgg tgcattcctg | 1780 |
| aactatatta attgttgagg gcctggagaa ccatgggaaa atgaactcag agctccatta | 1840 |
| atcttgatca ttccttctct ctctttctct ctctcttgtt ttaattactt tctcatcttt | 1900 |
| attcccctca acccctgaga cactgccata taccacaa accataaaca tcctccaatg | 1960 |
| acctagcccc atccctccat tcactcccag gtaagaattc agacaaatgt ccacagaggt | 2020 |
| tacagcatac gtacggttgt gttatatctc atatatgacc ccttcatgtc ctaaggaaga | 2080 |
| cattttctct tagaggtttt cattttagta tatcttaaaa gaatcttgtg ttaccttgcc | 2140 |
| tccatctttt tcttgggtaa ggactacact ttgtgtctct gatgttgctg ttcacagctt | 2200 |
| ttcttgatag gcctagtaca atcttgggaa cagggttgct gtgtggtgaa ggtctgacag | 2260 |
| tagttcttag tcttgcctat cttaggtagc tacgctgtgc attttattg gtatactatg | 2320 |
| aattgttcca gataccttca gtttggaaag ttttctgaga aatggagacg tcatgcggca | 2380 |
| tcaccttatt aaaatgcatt tgaagccttt t | 2411 |

<210> SEQ ID NO 8
<211> LENGTH: 99
<212> TYPE: PRT
<213> ORGANISM: Mus musculus

<400> SEQUENCE: 8

Gln Arg Gln Ser Arg Leu Val Arg Thr Ala Arg Gln Thr Leu Cys Cys
1               5                   10                  15

-continued

```
Val Gln Ile Gln Val Lys Gly Thr Lys Met Gln Ser Asn Lys Ala Phe
                20                  25                  30

Asn Leu Glu Lys Gln Asn His Thr Pro Arg Lys His Gln His His
            35                  40                  45

His Gln Gln His His Gln Gln Gln Gln Gln Gln Gln Gln Gln Pro
        50                  55                  60

Pro Pro Ile Pro Ala Asn Gly Gln Gln Ala Ser Ser Gln Asn Glu
65                  70                  75                  80

Gly Leu Thr Ile Asp Leu Lys Asn Phe Arg Lys Pro Gly Glu Lys Thr
                85                  90                  95

Phe Thr Gln
```

<210> SEQ ID NO 9
<211> LENGTH: 509
<212> TYPE: PRT
<213> ORGANISM: Homo sapiens

<400> SEQUENCE: 9

```
Met Gly Cys Ser Ala Lys Ala Arg Trp Ala Gly Ala Leu Gly Val
1               5                   10                  15

Ala Gly Leu Leu Cys Ala Val Leu Gly Ala Val Met Ile Val Met Val
                20                  25                  30

Pro Ser Leu Ile Lys Gln Gln Val Leu Lys Asn Val Arg Ile Asp Pro
            35                  40                  45

Ser Ser Leu Ser Phe Asn Met Trp Lys Glu Ile Pro Ile Pro Phe Tyr
        50                  55                  60

Leu Ser Val Tyr Phe Phe Asp Val Met Asn Pro Ser Glu Ile Leu Lys
65                  70                  75                  80

Gly Glu Lys Pro Gln Val Arg Glu Arg Gly Pro Tyr Val Tyr Arg Glu
                85                  90                  95

Phe Arg His Lys Ser Asn Ile Thr Phe Asn Asn Asn Asp Thr Val Ser
            100                 105                 110

Phe Leu Glu Tyr Arg Thr Phe Gln Phe Gln Pro Ser Lys Ser His Gly
        115                 120                 125

Ser Glu Ser Asp Tyr Ile Val Met Pro Asn Ile Leu Val Leu Gly Ala
    130                 135                 140

Ala Val Met Met Glu Asn Lys Pro Met Thr Leu Lys Leu Ile Met Thr
145                 150                 155                 160

Leu Ala Phe Thr Thr Leu Gly Glu Arg Ala Phe Met Asn Arg Thr Val
                165                 170                 175

Gly Glu Ile Met Trp Gly Tyr Lys Asp Pro Leu Val Asn Leu Ile Asn
            180                 185                 190

Lys Tyr Phe Pro Gly Met Phe Pro Phe Lys Asp Lys Phe Gly Leu Phe
        195                 200                 205

Ala Glu Leu Asn Asn Ser Asp Ser Gly Leu Phe Thr Val Phe Thr Gly
    210                 215                 220

Val Gln Asn Ile Ser Arg Ile His Leu Val Asp Lys Trp Asn Gly Leu
225                 230                 235                 240

Ser Lys Val Asp Phe Trp His Ser Asp Gln Cys Asn Met Ile Asn Gly
                245                 250                 255

Thr Ser Gly Gln Met Trp Pro Pro Phe Met Thr Pro Glu Ser Ser Leu
            260                 265                 270

Glu Phe Tyr Ser Pro Glu Ala Cys Arg Ser Met Lys Leu Met Tyr Lys
        275                 280                 285
```

-continued

```
Glu Ser Gly Val Phe Glu Gly Ile Pro Thr Tyr Arg Phe Val Ala Pro
    290                 295                 300
Lys Thr Leu Phe Ala Asn Gly Ser Ile Tyr Pro Pro Asn Glu Gly Phe
305                 310                 315                 320
Cys Pro Cys Leu Glu Ser Gly Ile Gln Asn Val Ser Thr Cys Arg Phe
                325                 330                 335
Ser Ala Pro Leu Phe Leu Ser His Pro His Phe Leu Asn Ala Asp Pro
            340                 345                 350
Val Leu Ala Glu Ala Val Thr Gly Leu His Pro Asn Gln Glu Ala His
        355                 360                 365
Ser Leu Phe Leu Asp Ile His Pro Val Thr Gly Ile Pro Met Asn Cys
370                 375                 380
Ser Val Lys Leu Gln Leu Ser Leu Tyr Met Lys Ser Val Ala Gly Ile
385                 390                 395                 400
Gly Gln Thr Gly Lys Ile Glu Pro Val Leu Pro Leu Leu Trp Phe
                405                 410                 415
Ala Glu Ser Gly Ala Met Glu Gly Glu Thr Leu His Thr Phe Tyr Thr
            420                 425                 430
Gln Leu Val Leu Met Pro Lys Val Met His Tyr Ala Gln Tyr Val Leu
        435                 440                 445
Leu Ala Leu Gly Cys Val Leu Leu Val Pro Val Ile Cys Gln Ile
450                 455                 460
Arg Ser Gln Glu Lys Cys Tyr Leu Phe Trp Ser Ser Lys Lys Gly
465                 470                 475                 480
Ser Lys Asp Lys Glu Ala Ile Gln Ala Tyr Ser Glu Ser Leu Met Thr
                485                 490                 495
Ser Ala Pro Lys Gly Ser Val Leu Gln Glu Ala Lys Leu
            500                 505
```

<210> SEQ ID NO 10
<211> LENGTH: 2603
<212> TYPE: DNA
<213> ORGANISM: Homo sapiens

<400> SEQUENCE: 10

```
cccggatcca ccgtgcctct gcggcctgcg tgcccggagt ccccgcctgt gtcgtctctg      60
tcgccgtccc cgtctcctgc caggcgcgga gccctgcgag ccgcgggtgg ccccaggcg     120
cgcagacatg gctgctccg ccaaagcgcg ctgggctgcc ggggcgctgg cgtcgcggg     180
gctactgtgc gctgtgctgg gcgctgtcat gatcgtgatg gtgccgtcgc tcatcaagca     240
gcaggtcctt aagaacgtgc gcatcgaccc cagtagcctg tccttcaaca tgtggaagga     300
gatccctatc cccttctatc tctccgtcta cttctttgac gtcatgaacc ccagcgagat     360
cctgaagggc gagaagccgc aggtgcggga gcgcgggccc tacgtgtaca gggagttcag     420
gcacaaaagc aacatcacct tcaacaacaa cgacaccgtg tccttcctcg agtaccgcac     480
cttccagttc cagcccttca gtcccacgg ctcggagagc gactacatcg tcatgcccaa     540
catcctggtc ttgggtgcgg cggtgatgat ggagaataag cccatgaccc tgaagctcat     600
catgaccttg gcattcacca ccctcggcga acgtgcctc atgaaccgca ctgtgggtga     660
gatcatgtgg ggctacaagg acccccttgt gaatctcatc aacaagtact tccaggcat     720
gttcccttc aaggacaagt tcggattatt tgctgagctc aacaactccg actctgggct     780
cttcacggtg ttcacggggg tccagaacat cagcaggatc cacctcgtgg acaagtggaa     840
cgggctgagc aaggttgact tctggcattc cgatcagtgc aacatgatca atggaacttc     900
```

```
tgggcaaatg tggccgccct tcatgactcc tgagtcctcg ctggagttct acagcccgga    960
ggcctgccga tccatgaagc taatgtacaa ggagtcaggg gtgtttgaag gcatccccac   1020
ctatcgcttc gtggctccca aaaccctgtt tgccaacggg tccatctacc cacccaacga   1080
aggcttctgc ccgtgcctgg agtctggaat tcagaacgtc agcacctgca ggttcagtgc   1140
ccccttgttt ctctcccatc ctcacttcct caacgccgac ccggttctgg cagaagcggt   1200
gactggcctg cacccctaacc aggaggcaca ctccttgttc ctggacatcc acccggtcac   1260
gggaatcccc atgaactgct ctgtgaaact gcagctgagc ctctacatga aatctgtcgc   1320
aggcattgga caaactggga agattgagcc tgtggtcctg ccgctgctct ggtttgcaga   1380
gagcggggcc atggaggggg agactcttca cacattctac actcagctgg tgttgatgcc   1440
caaggtgatg cactatgccc agtacgtcct cctggcgctg ggctgcgtcc tgctgctggt   1500
ccctgtcatc tgccaaatcc ggagccaaga gaaatgctat ttatttttgga gtagtagtaa   1560
aaagggctca aggataagg aggccattca ggcctattct gaatccctga tgacatcagc   1620
tcccaagggc tctgtgctgc aggaagcaaa actgtagggt cctgaggaca ccgtgagcca   1680
gccaggcctg gccgctgggc ctgaccggcc cccagcccc tacacccgc ttctcccgga   1740
ctctcccagc ggacagcccc ccagccccac agcctgagcc tcccagctgc catgtgcctg   1800
ttgcacacct gcacacacgc cctggcacac atacacacat gcgtgcaggc ttgtgcagac   1860
actcagggat ggagctgctg ctgaagggac ttgtagggag aggctcgtca acaagcactg   1920
ttctggaacc ttctctccac gtggcccaca ggcctgacca caggggctgt gggtcctgcg   1980
tccccttcct cgggtgagcc tggcctgtcc cgttcagccg ttgggcccag gcttcctccc   2040
ctccaaggtg aaacactgca gtcccggtgt ggtggctccc catgcaggac gggccaggct   2100
gggagtgccg ccttcctgtg ccaaattcag tggggactca gtcccaggc cctggccacg   2160
agctttggcc ttggtctacc tgccaggcca ggcaaagcgc ctttacacag gcctcggaaa   2220
acaatggagt gagcacaaga tgccctgtgc agctgcccga gggtctccgc ccaccccggc   2280
cggactttga tcccccccgaa gtcttcacag gcactgcatc gggttgtctg gcgcccttt   2340
cctccagcct aaactgacat catcctatgg actgagccgg ccactctctg gccgaagtgg   2400
ccgcaggctg tgcccccgag ctgcccccac cccctcacag ggtccctcag attataggtg   2460
cccaggctga ggtgaagagg cctggggggcc ctgccttccg ggcgctcctg gaccctgggg   2520
caaacctgtg acccttttct actggaatag aaatgagttt tatcatcttt gaaaaataat   2580
tcactcttga agtaataaac gtt                                            2603

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
caagaagcca agctgtaggg                                                  20

<210> SEQ ID NO 12
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 12
cccaacaggc tctactcagc                                               20

<210> SEQ ID NO 13
<211> LENGTH: 18
<212> TYPE: DNA
<213> ORGANISM: Artificial Sequence
<220> FEATURE:
<223> OTHER INFORMATION: Synthetic

<400> SEQUENCE: 13
tagacaagat ggtgaagg                                                 18

<210> SEQ ID NO 14
<211> LENGTH: 18
<212> TYPE: DNA
<213> ORGANISM: Artificial Sequence
<220> FEATURE:
<223> OTHER INFORMATION: Synthetic

<400> SEQUENCE: 14
tccttggagg ccatgtag                                                 18
```